US009163232B2

(12) United States Patent
Haurum et al.

(10) Patent No.: US 9,163,232 B2
(45) Date of Patent: Oct. 20, 2015

(54) METHOD FOR MANUFACTURING RECOMBINANT POLYCLONAL PROTEINS

(75) Inventors: John S. Haurum, København (DK); Finn C. Wiberg, Farum (DK); Vincent W. Coljee, Hellerup (DK); Jacqueline Sharon, Chestnut Hill, MA (US); Chiou-Ying Yang, Taichung (TW)

(73) Assignee: Symphogen A/S, Lyngby (DK)

( * ) Notice: Subject to any disclaimer, the term of this patent is extended or adjusted under 35 U.S.C. 154(b) by 579 days.

(21) Appl. No.: 12/339,490

(22) Filed: Dec. 19, 2008

(65) Prior Publication Data
US 2009/0136498 A1    May 28, 2009

Related U.S. Application Data

(63) Continuation of application No. 10/540,227, filed as application No. PCT/DK2004/000001 on Jan. 7, 2004, now abandoned.

(60) Provisional application No. 60/438,403, filed on Jan. 7, 2003, provisional application No. 60/476,018, filed on Jun. 5, 2003.

(30) Foreign Application Priority Data

Jan. 7, 2003 (DK) .................................. 2003 00008

(51) Int. Cl.
*C40B 50/06* (2006.01)
*C12N 15/10* (2006.01)
(Continued)

(52) U.S. Cl.
CPC ............ *C12N 15/1093* (2013.01); *C07K 16/18* (2013.01); *C07K 16/2833* (2013.01); *C07K 16/36* (2013.01); *C07K 16/40* (2013.01); *C07K 2317/55* (2013.01); *C40B 50/06* (2013.01)

(58) Field of Classification Search
None
See application file for complete search history.

(56) References Cited

U.S. PATENT DOCUMENTS 4,959,317 A * 9/1990 Sauer ............................ 435/462
5,654,182 A   8/1997 Wahl et al.
(Continued)

FOREIGN PATENT DOCUMENTS

EP   1 293 564   3/2003
EP   1 484 402   12/2004
(Continued)

OTHER PUBLICATIONS

Lu at al., "Tailoring in Vitro Selection for a Picomolar Affinity Human Antibody Directed against Vascular Endothelial Growth Factor Receptor 2 for Enhanced Neutralizing Activity," Journal of Biological Chemistry (2003), 278(44):43496-43507.
(Continued)

*Primary Examiner* — Christian Boesen
(74) *Attorney, Agent, or Firm* — Ropes & Gray LLP; Z. Ying Li; Ryan Murphey

(57) ABSTRACT

The invention relates to a method for manufacturing a recombinant polyclonal protein composition, in particular a recombinant polyclonal antibody composition. The method comprises obtaining a collection of cells transfected with a library of variant nucleic acid sequences, wherein each call in the collection is transfected with and capable of expressing one member of the library, which encodes a distinct member of a polyclonal protein that binds a particular antigen and which is located at the same single site in the genome of individual cells in said collection, wherein said nucleic acid sequence is not naturally associated with said cell in the collection. The cells are cultured under suitable conditions for expression of the polyclonal protein, which is obtained from the cells or culture supernatant. The present method is suitable for manufacturing recombinant polyclonal antibodies, thereby making available a superior replacement of plasma-derived therapeutic immunoglobulin products.

13 Claims, 12 Drawing Sheets

(51) Int. Cl.
  *C07K 16/18* (2006.01)
  *C07K 16/28* (2006.01)
  *C07K 16/36* (2006.01)
  *C07K 16/40* (2006.01)

(56) References Cited

U.S. PATENT DOCUMENTS

| | | | |
|---|---|---|---|
| 5,677,177 | A | 10/1997 | Wahl et al. |
| 5,789,208 | A | 8/1998 | Sharon |
| 6,111,166 | A | 8/2000 | van de Winkel |
| 6,368,821 | B1 | 4/2002 | Greener et al. |
| 6,610,472 | B1 | 8/2003 | Zhu et al. |
| 6,849,259 | B2 | 2/2005 | Haurum et al. |
| 7,262,028 | B2 * | 8/2007 | Van Berkel et al. ......... 435/69.6 |
| 7,850,965 | B2 | 12/2010 | Jensen et al. |
| 7,910,332 | B2 | 3/2011 | Nielsen et al. |
| 2002/0009453 | A1 | 1/2002 | Haurum et al. |
| 2002/0155114 | A1 | 10/2002 | Marks et al. |
| 2003/0044398 | A1 | 3/2003 | Robl et al. |
| 2005/0180967 | A1 | 8/2005 | Haurum et al. |
| 2005/1070398 | | 8/2005 | Van Berkel et al. |
| 2006/0275766 | A1 | 12/2006 | Haurum et al. |
| 2007/0141048 | A1 | 6/2007 | Oleksiewicz et al. |
| 2008/0069822 | A1 | 3/2008 | Jensen et al. |
| 2008/0131882 | A1 | 6/2008 | Rasmussen et al. |
| 2008/0206236 | A1 | 8/2008 | Haurum |
| 2009/0017017 | A1 | 1/2009 | Rasmussen et al. |
| 2009/0111142 | A1 | 4/2009 | Nielsen et al. |
| 2009/0136498 | A1 | 5/2009 | Haurum et al. |

FOREIGN PATENT DOCUMENTS

| | | |
|---|---|---|
| WO | WO91/16074 | 10/1991 |
| WO | WO 95/20401 A1 | 8/1995 |
| WO | WO98/37186 | 8/1998 |
| WO | WO-98/41645 | 9/1998 |
| WO | WO-01/05961 | 1/2001 |
| WO | WO 01/07572 | 2/2001 |
| WO | WO-01/89563 | 11/2001 |
| WO | WO-02/44361 | 6/2002 |
| WO | WO-00/11155 | 7/2002 |
| WO | WO-02/055718 | 7/2002 |
| WO | WO2004/009618 | 1/2004 |
| WO | WO2004/029284 | 4/2004 |
| WO | WO2005/042774 | 5/2005 |
| WO | WO2005/070962 | 8/2005 |
| WO | WO2006/007853 | 1/2006 |
| WO | WO2007/065433 | 6/2007 |
| WO | WO2007/101441 | 9/2007 |
| WO | WO2008/095504 | 8/2008 |
| WO | WO2008/145133 | 12/2008 |

OTHER PUBLICATIONS

Wu at al., "Cloning, isolation and characterization of human tumor in situ monoclonal antibodies," Cancer Immunol Immunother (2002), 51:79-90.
Sharon et al., "Construction of Polyclonal Antibody Libraries using Phage Display," Methods Mol. Biol., vol. 178 (2002), pp. 101-112.
Sauer, B., "Site-specific recombination: developments and applications," Curr. Opin. Biol., vol. 5 (1994) pp. 521-527.
Behboodi et al., "Health and Reproducticve Profiles of Malaria AntigenProducing Transgenic Goats Derived by Somatic Cell Nuclear Transfer," Cloning Stem Cells 7: 107-118 (2005).
Bouquin et al., "Human antiRhesus D IgG1 antibody produced in transgenic plants," Transgeneic Research 11: 115-122 (2002).
Bregenholt et al., "Recombinant Human Polyclonal Antibodies: A New Class of Therapeutic Antibodies Against Viral Infections," Curr. Pharm. Des. 12:2007-2015 (2006).
Gorman, et al., "Sitespecific Gene Targeting for Gene Expression in Eukaryotes," Biotech. 11:455-460 (2000).
Haurum and Bregensholt, "Recombinant polyclonal antibodies: Therapeutic antibody technologies come full circle," Idrugs 8:404-409 (2005).

Haurum, J.S., "Recombinant polyclonal antibodies: the next generation of antibody therapeutics?" Drug Discov. Today 11:655-660 (2006).
Hodges et al., "Generation of bovine transgenics using somatic cell nuclear transfer," Reproductive Biology Endocrinology 1:81 (2003).
Hood et al., "Monoclonal antibody manufacture in transgenic plants myths and realities," Current Opinion Biotechnology 13:630-635 (2002).
Houdebine, "Antibody manufacture in transgenic animals and comparisons with other systems," Curr. Opin. Biotech. 13:625-629 (2002).
Huang et al., "An efficient and targeted gene integration system for highlevel antibody expression," J. Imm. Meth. 322:28-39 (2007).
Kang et al., "Linkage of recognition and replication functions by assembling combinatorial antibody Fab libraries along phage surfaces," Proc. Natl. Acad. Sci. USA 88:4363-4366 (1991).
International Search Report for International Application PCT/DK2009/050094, mailed on Jul. 24, 2009, European Patent Office, Netherlands.
Jang et al., "An approach for producing transgenic cloned cows by nuclear transfer of cells transfected with human alpha 1 antitrypsin gene," Theriogenology 65:1800-1812 (2006).
Kito et al., "Construction of engineered CHO strains for highlevel production of recombinant proteins," Appl. Microbiol. Biotechnol. 60:442-448 (2002).
Kumpel et al, "Section 1 C: Assessment of the functional activities and IgG Fc receptor utilisation of 64 IgG Rh monoclonal antibodies," Transfus. Clin. Biol. 9:45-53 (2002).
Lai et al., "Creating genetically modified pigs by using nuclear transfer," Reproductive Biology Endocrinology 1:82 (2003).
Li et al., "Optimization of humanized IgGs in glycoengineered Pichia pastoris," Nat. Biotech. 24(2):210-215 (2006).
Logtenberg, "Antibody cocktails: nextgeneration biopharmaceuticals with improved potency," Trends in Biotech. 25:390-394 (2007).
Lonberg, "Human antibodies from transgenic animals," Nature Biotech. 23: 1117-1125 (2005).
Meijer et al., "Isolation of Human Antibody Repertoires with Preservation of the Natural Heavy and Light Chain Pairing," J. Mol. Biol. 358:764-772 (2006).
Nyssonen et al., "Efficient Production of Antibody Fragments by the Filamentous Fungus Trichoderma reesei," Nat. Biotech. 11:591-595 (1993).
Poulsen et al., "Kinetic, Affinity, and Diversity Limits of Human Polyclonal Antibody Responses against Tetanus Toxoid," J. Immunol. 179:3841-3850 (2007).
Roberts and Szostak, "RNApeptide fusions for the in vitro selection of peptides and proteins," Proc. Natl. Acad. Sci. USA 94:12297-12302 (1997).
Santora et al., "Characterization of maleuric acid derivatives on transgenic human monoclonal antibody due to postsecretional modifications in goat milk," Biomed Chromatogr. 20:843-856 (2006).
Sautter and Enekel, "Selection of high-producing CHO cells using NPT selection marker with reduced enzyme activity," Biotech. Bioeng. 89:530-538 (2005).
Schaffitzel et al., "Ribosome display: an in vitro method for selection and evolution of antibodies from libraries," J. Immunol. Meth. 231:1191135 (1999).
Sharon et al., "Recombinant Polyclonal Antibodies for Cancer Therapy," J. Cell. Biochem. 96:305-313 (2005).
Stirnadel et al., "Genetic analysis of IgG subclass responses against RESA and MSP2 of Plasmodium falciparum in adults in Papua New Guinea," Epidemiol. Infect. 124:153:162 (2000).
Stoger et al., "Antibody Production in Transgenic Plants," Meth. Mol. Biol. 248:301-318 (2004).
Tang et al., "High level expression of a functional human/mouse chimeric antiCD20 monoclonal antibody in milk of transgenic mice," Transgenic Res. 17(4):727-732 (2008).
Tolstrup et al., "Development of recombinant human polyclonal antibodies for the treatment of complex human diseases," Expert Opin. Biol, Ther. 6:905-912 (2006).
Ward et al., "Characterization of Humanized Antibodies Secreted by *Aspergillus niger*," Applied Env. Microbiol. 70:2567-2576 (2004).

(56) References Cited

OTHER PUBLICATIONS

Wiberg et al., "Production of TargetSpecific Recombinant Human Polyclonal Antibodies in Mammalian Cells," Biotechnol. Bioeng. 94:396-405 (2006).
Wurm, "Production of recombinant protein therapeutics in cultivated mammalian cells," Nature Biotech. 22(11):1393-1398 (2004).
Young et al., "Production of recombinant antibodies in the milk of transgenic animals," Res. Immunol. 149:609-610—(1998).
Zahra et al., "Selectable in-vivo recombination to increase antibody library size—an improved phage display vector system." Gene 227:49-54 (1999).
Zhu et al., "Production of human monoclonal antibody in eggs of chimeric chickens," Nature Biotech. 23:1159-1169 (2005).
Sugimura et al., "Phage display technology and human antibody engineering," DOJIN News 109:1-7 (2004) (English Abstract).
Biard-Piechaczyk et al., Human Antibodies, 9, 1999, pp. 67-77.
Boder et al., "Yeast Surface Display for Screening Combinatorial Polypeptide Libraries", Nature Biotechnology 15:553-557 (1997).
Boulot et al., "Crystallization and Preliminary X-ray Diffraction Study of the Bacterially Expressed Fv from the Monoclonal Anti-lysozyme Antibody D1.3 and of its Complex with the Antigen, Lysozyme", J. Mol. Biol. 213:617-619 (1990).
Brezinsky et al., "A Simple Method for Enriching Populations of Transfected CHO Cells for Cells of Higher Specific Productivity", Journal of Immunological Methods 277:141-155 (2003).
Canfield et al., "The Binding Affinity of Human IgG for its High AQffinity Fc Recptor is Determined by Multiple Amino Acids in the $C_h2$ Domain and is Modulated by the Hinge Region", J. Exp. Med. 173:1483-1491 (1991).
Cull et al., "Screening for Receptor Ligands using Large Libraries of Peptides Linked to the C Terminus of the lac Repressor", Proc. Natl. Acad. Sci 89:1865-1869 (1992).
Czerkinsky et al., "A Solid-Phase Enzyme-Linked Immunospot (ELISPOT) Assay for Enumeration of Specific Antibody-Secreting Cells", Journal of Immunological Mehtods 65:10-121 (1983).
Dreher et al., "Colony Assays for Antibody Fragments Expressed in Bateria", Journal of Immunological Methods 139:197-205 (1991).
Fuchs et al., "Targeting Recombinant Antibodies to the Surface of *Escherichia coli*: Fusion to a Peptidoglycan Associated Lipoprotein", Biotechnology 9:1369-1372 (1991).
Gorman et al., "Site-specific Gene Targeting for Gene Expression in Eukaryotes", Biotechnology 11:455-460 (2000).
Grabherr et al., "The Baculovirus Expression System as a Tool for Generating Diversity by Viral Surface Display", Combinatorial Chemistry & High Throughput Screening 4:185-192 (2001).
Kuroiwa et al., "Cloned Transchromosomic Calves Producing Human Immunoglobin", Nature Biotechnology 20:889-893 (2002).
Soderlind et al., "Recombing Germline-derived CDR Sequences for Creating Diverse Single-Framework Antibody Libraries", Nature Biotechnology 18:852-856 (2000).
Tsurushita et al., Gene 172, 1999, 59-63.
Verhoeyen et al., "Evaluation of Retroviral Vector Design in Defined Chromosomal Loci by Flp-Mediated Cassette Replacement", Human Gene Therapy 12:933-944 (2001).
Zahra et al., Gene, 227, 1999, pp. 49-54.

* cited by examiner

Fragment of promoter cassette (mammalian)
1433 bp (molecule 6135 bp)

Step 1 ↓ digest with SacI + XhoI, ligate fragments from A and B, to generate symvc12

Continued

Figure 4 continued
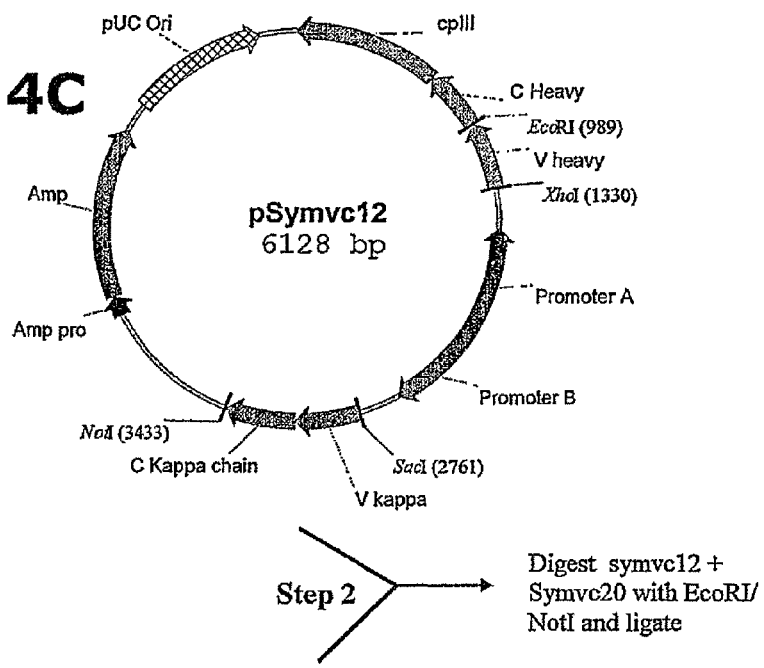
Fig. 4C
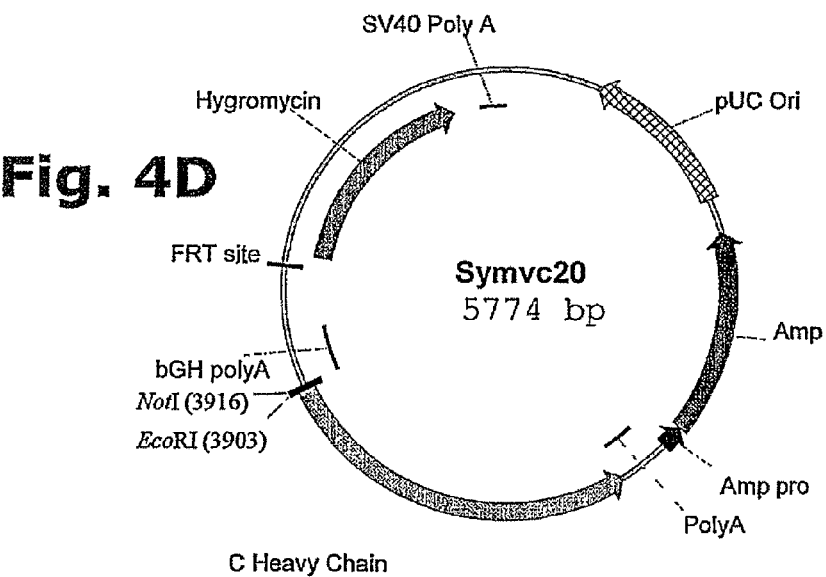
Fig. 4D 16 days 34 days

```
                               SEQUENCE LISTING

<160> NUMBER OF SEQ ID NOS: 7

<210> SEQ ID NO 1
<211> LENGTH: 48
<212> TYPE: DNA
<213> ORGANISM: Saccharomyces cerevisiae

<400> SEQUENCE: 1
gaagttccta ttccgaagtt cctattctct agaaagtata ggaacttc                   48

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcattgacag gaggttgagg c                                                21

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctgccgacc gctgctgctg gtc                                              23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcattgacag gaggttgagg c                                                21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtgtccactc tgaggttcag                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 6
caaatagccc ttgaccaggc                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtgtccactc tgaggttcag                                              20
```

METHOD FOR MANUFACTURING RECOMBINANT POLYCLONAL PROTEINS

CROSS-REFERENCE TO RELATED APPLICATIONS

The present application is a continuation of U.S. application Ser. No. 10/540,227, filed Jan. 7, 2004, which is the U.S. National Stage of PCT/DK2004/000001 (WO 2004/061104A2) filed Jan. 7, 2004, which was published in English, and which claims priority to Danish Patent Application No. PA2003/00008, filed Jan. 7, 2003, U.S. Provisional Application Nos.: 60/438,403, filed Jan. 7, 2003, and 60/476,018, filed Jun. 5, 2003; the entire contents of each of which are incorporated herein by reference.

FIELD OF THE INVENTION

The present invention forms the basis of a technology platform for producing recombinant polyclonal proteins, such as proteins from the immunoglobulin superfamily, soluble or membrane-bound forms of B or T cell receptors, to be used as a new class of therapeutic in the treatment, amelioration or prevention of various infections, inflammatory diseases, transplantation rejection, cancer, and allergies.

BACKGROUND OF THE INVENTION

A number of infectious diseases and cancers lacks efficient therapies. Monoclonal antibodies have generally not been successful against these targets, partly due to variability of the complex targets and adaptive mutations of target proteins causing immune escape from monoclonal antibody recognition. Polyclonal antibodies on the other hand are able to target a plurality of dynamic targets, e.g., on viruses or cancer cells. Also, polyclonal antibodies have the highest probability of retaining activity in the event of antigenic mutation.

Different commercially available polyclonal antibody therapeutics exist including: 1) normal human immunoglobulin isolated from the blood of normal human donors; 2) human hyperimmune immunoglobulin derived from the blood of individual human donors carrying antibodies against a particular disease target, e.g., a virus, which they previously have encountered either through infection or vaccination; and 3) animal hyperimmune immunoglobulin derived from the blood of immunized animals.

Immunoglobulin purified from human blood has proved effective against infections with hepatitis B virus, respiratory syncytial virus, cytomegalovirus and other herpes viruses, rabies virus, botulinum toxin, etc, as well as in the neonatal rhesus D prophylaxis. Immunoglobulin purified from the blood of rabbits immunized with human T cells is used to afford T cell immunosuppression in the treatment or prevention of transplant rejection (e.g., Thymoglobulin). Normal human immunoglobulin has been utilized to boost the immune system of immunodeficient patients, as well as in the therapy of various autoimmune disorders.

Nevertheless, widespread immunoglobulin use has been limited due to the constrained supply of donor blood raw material, problems with batch-to-batch variations, and variable safety. Animal-derived immunoglobulins in particular are faced with the same problems of immunogenicity as was observed for animal-derived monoclonal antibodies in the 1980s and 1990s. Finally, as with other blood products, the risk of transmission of infectious agents such as HIV, herpes or hepatitis viruses or prions remains. Accordingly, while clinicians acknowledge that polyclonal antibodies are a preferred therapeutic in some situations, their use has been very limited.

New approaches to generate human immunoglobulins arose with the transgenic animal techniques. Transgenic mice carrying human immunoglobulin loci have been created (U.S. Pat. No. 6,111,166). These mice produce fully human immunoglobulins, and antibodies against a specific target can be raised by usual immunization techniques. However, larger antibody yields are limited because of the relatively small size of mice. Larger animals have also been made transgenic for the human immunoglobulin genes, e.g., cows, sheep, rabbits, and chickens (Kurolwa, Y. et al. *Nature Biotechnology;* 2002; 20: 889-893). However, producing polyclonal antibodies for therapy from the blood of such animals is not without complications. First, the immunophysiology of the animal and humans may display considerable differences, causing a difference in the resulting immune repertoire, functional rearrangement, and diversity of the antibody response. Second, mitotic instability of the introduced immunoglobulin loci might influence the long-term production of antibodies. Third, it is technically challenging to delete the animal's own immunoglobulin loci so that e.g., the animal antibody production will not exceed the production of human antibody. Fourth, the risk of transmission of infectious agents such as viruses, prions or other pathogens accompanies the administration of human antibodies produced in animals.

Accordingly, there is a need for manufacturing technologies for producing recombinant polyclonal proteins, such as antibodies, in sufficiently large amounts and with minimal batch-to-batch variations for safe clinical uses. Efficient methods for manufacturing homogenous recombinant proteins using eukaryotic (in particular mammalian) expression cell lines have been developed for the production of a variety of proteins including monoclonal antibodies, interleukins, interferons, tumor necrosis factor, coagulation factors VII, VIII and IX. Many of these techniques are based on transfection and random integration of the gene of interest into the genome of the expression cell line followed by selection, amplification, and characterization of a high-producer expression clone and propagation of this clone as a master expression cell line.

The expression of an inserted foreign gene may be influenced by "position effects" from surrounding genomic DNA. In many cases, the gene is inserted into sites where the position effects are strong enough to inhibit the synthesis of the product of the introduced gene. Furthermore, the expression is often unstable due to silencing mechanisms (i.e. methylation) imposed by the surrounding chromosomal host DNA.

Systems allowing integration and expression of a gene of interest in mammalian cells at a specific genomic location have been developed for the expression of a homogenous recombinant protein composition (U.S. Pat. Nos. 4,959,317 and 5,654,182; WO 98/41645; WO 01/07572). WO 98/41645 describes the site-specific integration for production of a mammalian cell line that secretes, for example, antibody. However, this expression is monoclonal and there is no indication that transfections could be done with a library of vectors. Nor are there any suggestions how to maintain the original diversity generated by specific $V_H$-$V_L$ combinations in a library.

DISCLOSURE OF CONTRIBUTION

The present invention provides solutions for generating a manufacturing cell line for expression and production of a recombinant polyclonal protein, avoiding significant bias among the individual members constituting the polyclonal protein.

Further, the present invention does not utilize animals in the polyclonal protein production, thereby obviating the ethical and clinical difficulties associated with such approaches.

SUMMARY OF THE INVENTION

The present invention provides methods for producing a recombinant polyclonal manufacturing cell line for the production of a recombinant polyclonal protein, often selected from the immunoglobulin superfamily. Especially the production of polyclonal antibodies, polyclonal T cell receptors or polyclonal fragments thereof are of interest. The present invention allows for the commercial production of a recombinant polyclonal protein for use in pharmaceutical compositions. One important feature of the invention is that during the manufacturing process biased expression of the individual molecules constituting the polyclonal protein is kept to a non-significant level, minimizing unwanted batch-to-batch variation.

One aspect of the present invention relates to a method for manufacturing a recombinant polyclonal protein of interest, wherein said polyclonal protein comprises (or consists of) distinct members that bind a particular antigen, said method comprising: a) providing a collection of cells comprising a library of variant nucleic acid sequences, where each of said nucleic acid sequences encodes a distinct member of said polyclonal protein and where each of said nucleic acid sequences are integrated at the same, single site of the genome of each individual cell in said collection of cells; b) culturing said collection of cells under conditions facilitating expression of said polyclonal protein; and c) recovering said expressed polyclonal protein from the cell culture, cell fraction or cell culture medium.

A further aspect of the present invention relates to a method for generating a collection of cells suitable as a recombinant polyclonal manufacturing cell line, said method comprising: a) providing a library of vectors comprising a population of variant nucleic acid sequences, wherein each of said vectors comprises 1) one single copy of a distinct nucleic acid sequence encoding a distinct member of a polyclonal protein comprising (or consisting of) distinct members that bind a particular antigen and 2) one or more recombinase recognition sequences; b) introducing said library of vectors into a host cell line, wherein the genome of each individual cell of said host cell line comprises recombinase recognition sequences, matching those of the vector, at a single specific site in its genome; c) ensuring the presence in said cells of one or more recombinases so that the variant nucleic acid sequences of step (a) are integrated site-specifically in the cells of the host cell line, where said one or more recombinases is/are either i) expressed by said cells into which said nucleic acid sequence is introduced; ii) operatively encoded by the vectors of step a; iii) provided through expression from a second vector; or iv) provided to the cell as a protein; and d) selecting cells comprising an integrated copy from said library of variant nucleic acid sequences.

In both methods of the invention, it will be understood that the polyclonal protein normally is one that is not naturally associated with the cells wherein expression is effected.

The present invention describes several methods by which a library of variant nucleic acid sequences can be introduced into a host cell line in order to generate a collection of cells suitable as polyclonal manufacturing cell line. These methods include bulk transfection of a collection of cells with the library, semi-bulk transfection of aliquots of cells with fractions of the library or individual transfection where host cells are transfected with individual members of the library followed by pooling of the clones generated upon selection. Preferably the present invention utilizes mammalian cells (cell lines or cell types) as host cell line.

In one aspect of the invention, the individual members of a polyclonal protein are encoded from pairs of independent gene segments. Polyclonal proteins, where the individual members are comprised of two polypeptide chains, include soluble or membrane-bound forms of antibodies and T cell receptors. In further embodiments of the present invention a pair of gene segments encode an antibody heavy chain and light chain variable region, or a T cell receptor alpha chain and beta chain variable region or a T cell receptor gamma chain and delta chain variable region.

The present invention further provides a recombinant polyclonal manufacturing cell line comprising a collection of cells transfected with a library of variant nucleic acid sequences, wherein each cell in the collection is transfected with and capable of expressing one member of the library, which encodes a distinct member of a polyclonal protein that binds a particular antigen and which is located at the same single site in the genome of individual cells in said collection, wherein said nucleic acid sequence is not naturally associated with said cell in the collection. The cell line preferably originates from a mammalian cell line such as Chinese hamster ovary (CHO) cells, COS cells, BHK cells, myeloma cells (e.g., Sp2/0 cells, NS0), YB2/0, NIH 3T3, fibroblast or immortalized human cells such as HeLa cells, HEK 293 cells, or PER.C6. However, non-mammalian eukaryotic or prokaryotic cells, such as plant cells, insect cells, yeast cells, bacteria, fungi etc., can also be used.

Also embraced by the present invention is a library of vectors for site-specific integration comprising a population of naturally occurring variant nucleic acid sequences, wherein each of said vectors comprises 1) one copy of a distinct nucleic acid sequence encoding a distinct member of a polyclonal protein that binds a particular antigen and 2) one or more recombinase recognition sequences.

In another aspect, the invention provides a pharmaceutical composition comprising, as an active ingredient, a recombinant polyclonal antibody (or fragment thereof) or polyclonal T cell receptor (or fragment thereof), preferably obtained by the methods of the invention. The recombinant polyclonal protein of the composition is specific for or reactive against a predetermined disease target. Such pharmaceutical compositions can be used for the treatment, amelioration or prevention of diseases such as cancer, infections, inflammatory diseases, allergy, asthma and other respiratory diseases, autoimmune diseases, immunological malfunctions, cardiovascular diseases, diseases in the central nervous system, metabolic and endocrine diseases, transplant rejection, or undesired pregnancy, in a mammal such as a human, a domestic animal, or a pet.

Definitions

By "protein" or "polypeptide" is meant any chain of amino acids, regardless of length or post-translational modification. Proteins can exist as monomers or multimers, comprising two or more assembled polypeptide chains, fragments of proteins, polypeptides, oligopeptides, or peptides.

As used herein, the term "polyclonal protein" or "polyclonality" refers to a protein composition comprising different, but homologous protein molecules, preferably selected from the immunoglobulin superfamily. Thus, each protein molecule is homologous to the other molecules of the composition, but also contains one or more stretches of variable polypeptide sequence, which is/are characterized by differences in the amino acid sequence between the individual members of the polyclonal protein. Known examples of such polyclonal proteins include antibody or immunoglobulin molecules, T cell receptors and B cell receptors. A polyclonal protein may consist of a defined subset of protein molecules, which has been defined by a common feature such as the shared binding activity towards a desired target, e.g., in the case of a polyclonal antibody against the desired target antigen.

The term "polyclonal protein of interest" covers a defined polyclonal protein subset, which shares a common feature, such as binding activity towards a desired target, e.g., in the case of polyclonal antibodies described by the binding activity or specificity against the target antigen, said antigen being one or more of e.g., separate proteins, microorganisms, parasites, cell types, allergens, or carbohydrate molecules, or any other structures, molecules, or substances, which may be the target of specific antibody binding, or mixtures of said antigens.

The terms "one member of a recombinant polyclonal protein composition" or "one member of a recombinant polyclonal protein" denote one protein molecule of a protein composition comprising different, but homologous protein molecules, where each protein molecule is homologous to the other molecules of the composition, but also contains one or more stretches of variable polypeptide sequence, which is/are characterized by differences in the amino acid sequence between the individual members of the polyclonal protein.

The terms "variable polypeptide sequence" and "variable region" are used interchangeably.

The terms "a distinct member of a recombinant polyclonal protein" denotes one protein molecule of a protein composition comprising different, but homologous protein molecules, where each protein molecule is homologous to the other molecules of the composition, but also contains one or more stretches of variable polypeptide sequence, which is/are characterized by differences in the amino acid sequence between the individual members of the polyclonal protein.

The term "antibody" describes a functional component of serum and is often referred to either as a collection of molecules (antibodies or immunoglobulin) or as one molecule (the antibody molecule or immunoglobulin molecule). An antibody molecule is capable of binding to or reacting with a specific antigenic determinant (the antigen or the antigenic epitope), which in turn may lead to induction of immunological effector mechanisms. An individual antibody molecule is usually regarded as monospecific, and a composition of antibody molecules may be monoclonal (i.e., consisting of identical antibody molecules) or polyclonal (i.e., consisting of different antibody molecules reacting with the same or different epitopes on the same antigen or even on distinct, different antigens). Each antibody molecule has a unique structure that enables it to bind specifically to its corresponding antigen, and all natural antibody molecules have the same overall basic structure of two identical light chains and two identical heavy chains. Antibodies are also known collectively as immunoglobulins. The terms antibody or antibodies as used herein are also intended to include chimeric and single chain antibodies, as well as binding fragments of antibodies, such as Fab, Fv fragments or scFv fragments, as well as multimeric forms such as dimeric IgA molecules or pentavalent IgM.

The term "polyclonal antibody" describes a composition of different antibody molecules which is capable of binding to or reacting with several different specific antigenic determinants on the same or on different antigens. Usually, the variability of a polyclonal antibody is thought to be located in the so-called variable regions of the polyclonal antibody. However, in the context of the present invention, polyclonality can also be understood to describe differences between the individual antibody molecules residing in so-called constant regions, e.g., as in the case of mixtures of antibodies containing two or more antibody isotypes such as the human isotypes IgG1, IgG2, IgG3, IgG4, IgA1, and IgA2, or the murine isotypes IgG1, IgG2a, IgG2b, IgG3, and IgA.

A "recombinant polyclonal antibody of interest" describes a defined recombinant polyclonal antibody subset, which is characterized by the ability to bind to a desired target or desired set of targets, said targets being e.g., a separate protein, a microorganism, a parasite, a cell, an allergen, or a carbohydrate molecule, or another structure, molecule, or substance which may be the target of specific antibody binding, or mixtures thereof.

The term "immunoglobulin" commonly is used as a collective designation of the mixture of antibodies found in blood or serum, but may also be used to designate a mixture of antibodies derived from other sources.

The term "immunoglobulin molecule" denotes an individual antibody molecule, e.g., as being a part of immunoglobulin, or part of any polyclonal or monoclonal antibody composition.

When stating that a member of a polyclonal protein binds to an antigen, it is herein meant a binding having binding constant that is below 1 mM, preferably below 100 nM, even more preferred below 10 nM.

The term "a library of variant nucleic acid molecules of interest" is used to describe the collection of nucleic add molecules, which collectively encode a "recombinant polyclonal protein of interest". When used for transfection, the library of variant nucleic acid molecules of interest is contained in a library of expression vectors. Such a library typically have at least 3, 5, 10, 20, 50, 1000, $10^4$, $10^5$ or $10^6$ distinct members.

As used herein the terms "one copy of a distinct nucleic acid sequence of interest" are not to be taken literally as a single stretch of nucleic acids corresponding to a single gene segment, but rather as one copy of all the gene segments required to produce all the subunits of one molecule of the protein of interest, and assembled into one nucleic acid molecule such as e.g. a vector. Some examples, where more than one gene segment usually is required to give rise to a complete molecule of a protein of interest include B cell receptors, antibodies and fragments of antibodies such as Fab's and variable domains, or T cell receptors. When introduced into the cell, the gene segments, which together encode the fully assembled protein of interest, reside in the same vector, thus being linked together in one nucleic acid sequence, possibly as separate transcriptional elements under control of different promoters.

The term "a gene of interest" as used herein, refer to a nucleic acid sequence composed of one or more gene segments (genomic or cDNA) that encode one member of a protein of interest. The plural form "genes of interest" refers to a library of nucleic acid sequences encoding a polyclonal protein of interest. The term "GOI" is used as an abbreviation of (a) gene(s) of interest.

As used herein, the term "vector" refers to a nucleic acid molecule into which a nucleic acid sequence can be inserted for transport between different genetic environments and/or for expression in a host cell. A vector capable of integrating into the genome of a host cell at a pre-determined, specific locus in the genome is herein named "a vector for site-specific integration". If the vector carries regulatory elements for transcription of the nucleic acid sequence inserted in the vector (at least a suitable promoter), the vector is herein called "an expression vector". If the expression vector is capable of integrating at a pre-determined, specific locus in the genome of the host cell, the expression vector may be called "an expression vector for site-specific integration". If the nucleic acid sequence inserted into the above identified vectors encodes a protein of interest as herein defined, the following terms are used "vector of interest", "vector of interest for site-specific integration", "expression vector of interest" and "expression vector of interest for site-specific integration". The term "an isotype-encoding vector" refers to a vector carrying nucleic acid sequences encoding an antibody isotype. In the present specification, "phagemid vector" and "phage vector" are used interchangeably. The terms "plasmid" and "vector" are used interchangeably. The invention is intended to include such other forms of vectors, which serve equivalent functions for example plasmids, phagemids and virus genomes or any nucleic acid molecules capable of directing the production of a desired protein in a proper host.

The term "each member of the library of vectors of interest" is used to describe individual vector molecules with a distinct nucleic acid sequence derived from a library of vectors of interest, where the nucleic acid sequence encodes for one member of the recombinant polyclonal protein of interest.

The term "mass transfer" is used to describe the transfer of nucleic acid sequences of interest from one population of vectors to another population of vectors and doing so for each DNA simultaneously without resorting to isolation of the individual DNA's of interest. Such populations of vectors can be libraries containing for example variable regions, promoters, leaders or enhancing elements of interest. These sequences can then be moved without prior isolation from for example a phage vector to a mammalian expression vector. Especially for antibody sequences this technique ensures that the linkage between $V_H$ and $V_L$ diversity is not lost while moving libraries from, for example, a selection vector (e.g., a phage display vector) to a mammalian expression vector. Hereby the original pairing of $V_H$ and $V_L$ is retained.

The term "transfection" is herein used as a broad term for introducing foreign DNA into a cell. The term is also meant to cover other functional equivalent methods for introducing foreign DNA into a cell, such as e.g., transformation, infection, transduction or fusion of a donor cell and an acceptor cell.

The term "selection" is used to describe a method where cells have acquired a certain characteristic that enable the isolation from cells that have not acquired that characteristic. Such characteristics can be resistance to a cytotoxic agent or production of an essential nutrient, enzyme, or color.

The terms "selectable marker gene", "selection marker gene", "selection gene" and "marker gene" are used to describe a gene encoding a selectable marker (e.g., a gene conferring resistance against some cytotoxic drug such as certain antibiotics, a gene capable of producing an essential nutrient which can be depleted from the growth medium, a gene encoding an enzyme producing analyzable metabolites or a gene encoding a colored protein which for example can be sorted by FACS) which is co-introduced into the cells together with the gene(s) of interest.

The term "recombinant protein" is used to describe a protein that is expressed from a cell line transfected with an expression vector comprising the coding sequence of the protein.

As used herein, the term "operably linked" refers to a segment being linked to another segment when placed into a functional relationship with the other segment. For example, DNA encoding a signal sequence is operably linked to DNA encoding a polypeptide if it is expressed as a leader that participates in the transfer of the polypeptide to the endoplasmic reticulum. Also, a promoter or enhancer is operably linked to a coding sequence if it stimulates the transcription of the sequence.

The term "a majority of the individual cells" refers to a percentage of the cells such as more than 80%, preferably more than 85%, more preferably 90%, 95%, or even 99% or higher.

As used herein, the term "genome" is not to be taken literally as the normal complement of chromosomes present in a cell, but also extra-chromosomal elements that can be introduced into and maintained in a cell. Such extra-chromosomal elements can include, but are not limited to, mini-chromosomes, YACs (yeast artificial chromosomes), MACs (mouse artificial chromosomes), or HACs (human artificial chromosomes).

The term "promoter" refers to a region of DNA involved in binding the RNA polymerase to initiate transcription.

The term "head-to-head promoters" refers to a promoter pair being placed in close proximity so that transcription of two gene fragments driven by the promoters occurs in opposite directions. A head-to-head promoter can also be constructed with a stuffer composed of irrelevant nucleic acids between the two promoters. Such a stuffer fragment can easily contain more than 500 nucleotides.

An "antibiotic resistance gene" is a gene encoding a protein that can overcome the inhibitory or toxic effect that an antibiotic has on a cell ensuring the survival and continued proliferation of cells in the presence of the antibiotic.

The term "internal ribosome entry site" or "IRES" describes a structure different from the normal 5' cap-structure on an mRNA. Both structures can be recognized by a ribosome to initiate scanning for an AUG codon to initiate translation. By using one promoter sequence and two initiating AUG's, a first and a second polypeptide sequence can be translated from a single mRNA. Thus, to enable co-translation of a first and a second polynucleotide sequence from a single bi-cistronic mRNA, the first and second polynucleotide sequence can be transcriptionally fused via a linker sequence including an IRES sequence that enables translation of the polynucleotide sequence downstream of the IRES sequence. In this case, a transcribed bi-cistronic RNA molecule will be translated from both the capped 5' end and from the internal IRES sequence of the bi-cistronic RNA molecule to thereby produce both the first and the second polypeptide.

The term "inducible expression" is used to describe expression that requires interaction of an inducer molecule or the release of a co-repressor molecule and a regulatory protein for expression to take place.

The term "constitutive expression" refers to expression which is not usually inducible.

The term "recombinase" refers to an enzyme that catalyses recombination between two or more recombination sites. Recombinases useful in the present invention catalyze recombination at specific recombination sites that are specific nucleic acid sequences recognized by a particular recombinase.

The term "scrambling" describes situations where two or more distinct members of a polyclonal protein comprised of two different polypeptide chains, e.g. from the immunoglobulin superfamily, is expressed from an individual cell. This situation may arise when the individual cell has integrated, into the genome, more than one pair of gene segments, where each pair of gene segments encode a distinct member of the polyclonal protein. In such situations unintended combinations of the polypeptide chains expressed from the gene segments can be made. These unintended combinations of polypeptide chains might not have any therapeutic effect.

The term "$V_H$-$V_L$ chain scrambling" is an example of the scrambling defined above. In this example the $V_H$ and $V_L$ encoding gene segments constitute a pair of gene segments. The scrambling occurs when unintended combinations of $V_H$ and $V_L$ polypeptides are produced from a cell where two different $V_H$ and $V_L$ encoding gene segment pairs are integrated into the same cell. Such a scrambled antibody molecule is not likely to retain the original specificity, and thus might not have any therapeutic effect.

The term "recombinant polyclonal manufacturing cell line" refers to a population of protein expressing cells that are transfected with a library of variant nucleic acid sequences of interest such that the individual cells, which together constitute the recombinant polyclonal manufacturing cell line, carry only one copy of a distinct nucleic acid sequence of interest, which encodes one member of the recombinant polyclonal protein of interest, and that each copy is integrated into the same site of the genome of each cell. The cells constituting the recombinant polyclonal manufacturing cell line are selected for their ability to retain the integrated copy of the distinct nucleic acid sequence of interest, for example by antibiotic selection. Cells which can constitute such a manufacturing cell line can be for example bacteria, fungi, eukaryotic cells, such as yeast, insect cells or mammalian cells, especially immortal mammalian cell lines such as CHO cells, COS cells, BHK cells, myeloma cells (e.g., Sp2/0 cells, NS0), NIH 3T3, YB2/ and immortalized human cells, such as HeLa cells, HEK 293 cells, or PER.C6.

The term "hot spot" as in "hot spot cell line" refers to a pre-established locus of the genome of the cell that has been selected or generated and characterized for highly efficient transcription of an integrated nucleic acid sequence of interest upon integration of the expression vector into that site.

The term "bias" is used to denote the phenomenon during recombinant polyclonal protein production, wherein the composition of a polyclonal vector, polyclonal cell line, or polyclonal protein alters over time due to random genetic mutations, differences in proliferation kinetics between individual cells, differences in expression levels between different expression construct sequences, or differences in the cloning efficiency of DNA.

The term "RFLP" refers to "restriction fragment length polymorphism", a method whereby the migratory gel pattern of nucleic acid molecule fragments are analyzed after cleavage with restriction enzymes.

The term "HDS" refers to a high density screening method where many discrete molecules are tested in parallel on membranes so that large numbers of test compounds are screened for a given activity simultaneously.

As used herein, "TaqMan PCR" refers to a PCR assay based on the TaqMan system described by Holland, P. M. et al., Proc. Natl. Acad. Sci. U.S.A. 88: 7276-7280 (1991).

The term "5' UTR" refers to a 5' untranslated region of the mRNA.

The term "Pfu PCR" refers to a PCR reaction carried out using a Pfu DNA polymerase (isolated from *Pyrococcus furiosus*), which is utilized because it has the highest fidelity among known thermostable polymerases.

Abbreviations: "CMV"=(human) Cytomegaio Virus. "MSPSV" Myeloproliferative Sarcoma Virus. "AdMLP"=Adenovirus Major Late Promoter. SV40 poly A=Simian Virus 40 poly A signal sequence. GFP=Green Flourescent Proteins. PVDF=polyvinylidene difluorid. TcR=T cell receptor; ELISA=Enzyme-Linked Immunosorbent Assay. LTR=Long Terminal Repeat.

Step 1: By restriction digestion with SacI and XhoI, the bacterial promoter cassette can be excised from pSymvc10 and by ligation, replaced with a mammalian promoter cassette (B) that has also been prepared by restriction digestion with SacI and XhoI.

(C) Schematic representation of a phagemid vector, pSymvc12, carrying sequences from the GOI, after promoter exchange with a mammalian head-to-head promoter cassette. Promoter A/Promoter B=head-to-head promoter cassette of choice (e.g., CMV/MPSV). V kappa=sequence encoding for a variable kappa light chain of a GOI. C Kappa chain=Sequence coding for the mouse constant kappa chain. V heavy=sequence encoding for a variable heavy chain of a GOI. C heavy chain=Sequence coding for the constant heavy chain CH1 domain. Restriction enzyme sites: NotI, SacI, XhoI and EcoRI. cpIII=phage protein III. Amp pro=A promoter allowing expression of the ampicillin resistance gene. Amp=An ampicillin resistance gene. pUC Ori=A pUC origin of replication.

Step 2: By restriction digestion of pSymvc12 with EcoRI and NotI, a nucleic acid fragment containing the whole of the kappa, promoter cassette and V heavy can be excised from pSymvc12 and ligated into an isotype-encoding vector, for example pSymvc20 (D), that has also been prepared by restriction digestion with EcoRI and NotI, thereby generating the mammalian expression vector pSymvc21 (E).

(E) Schematic representation of a mammalian expression vector, pSymvc21, with the variable heavy and kappa regions from the GOI, for antibody expression. This mammalian expression vector comprises the following elements: Amp pro=A promoter allowing expression of the ampicillin resistance gene. Amp=An ampicillin resistance gene. pUC Ori=A pUC origin of replication. Restriction enzyme sites: NotI and EcoRI. Promoter A/Promoter B=head-to-head promoter cassette of choice (e.g., CMV/MPSV). V kappa=V kappa sequence encoding for a variable kappa light chain of a GOI. C Kappa chain=Sequence coding for a mammalian constant kappa light chain (e.g., a mouse constant kappa chain). V heavy=V heavy sequence coding for a variable heavy chain of a GOI. C heavy chain=Sequences coding for a mammalian constant heavy chain (e.g., the sequences for mouse IgG1 or IgG2B constant heavy chain), R-B-globin pA=A Rabbit β-globin poly A sequence. bGH poly A=Bovine Growth Hormone poly A sequence. FRT site=A FRT recombination site. Hygromycin=gene for hygromycin resistance. SV40 poly A=SV40 poly A sequence sequence.

Figure 4A:
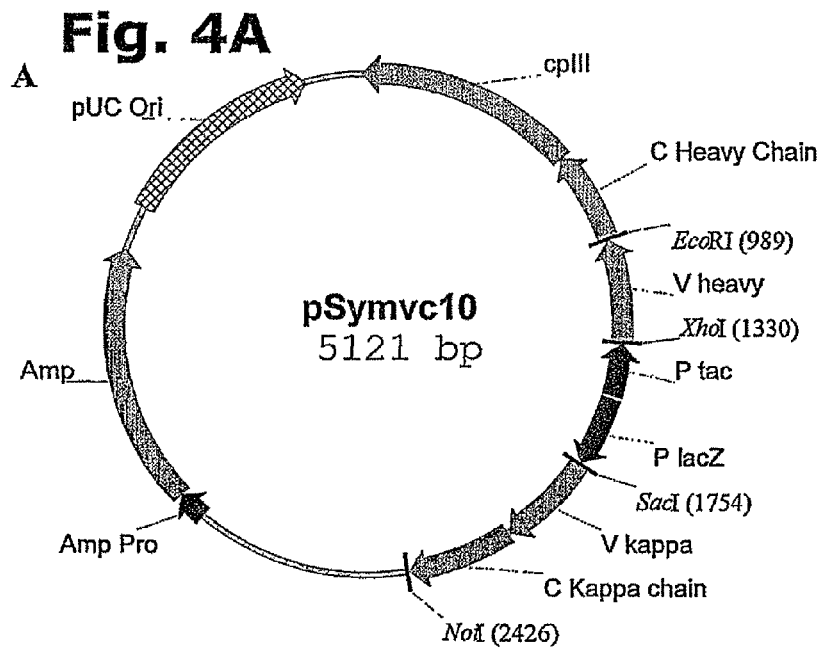
FIG. 4: Flow chart illustrating the generation of a mammalian expression vector. (A). A schematic representation of a phagemid vector, pSymvc10, which carries a sequence encoding a member of the GOI. P tac and P lacz=bacterial head-to-head promoter cassette. V kappa=sequence encoding a variable kappa light chain of a GOI. C Kappa chain=Sequence coding for the mouse constant kappa light chain. V heavy=a sequence encoding a variable heavy chain of a GOI. C heavy chain=Sequence coding for the constant heavy chain CH1 domain. Restriction enzyme sites: EcoRI, NotI, SacI and XhoI. cpIII=phage protein III. Amp pro=A promoter allowing expression of the ampicillin resistance gene. Amp=An ampicillin resistance gene. pUC Ori=A pUC origin of replication.
Figure 4B:

Naturally, the order of steps 1 and 2 can be reversed such that a fragment from pSsymvc10 containing the whole of the kappa, bacterial promoter cassette and V heavy can be excised from pSymvc10 using EcorI and NotI restriction digestion, which can then be ligated into an isotype-encoding vector, for example pSymvc20. The promoter exchange can then be performed on pSymvc20 by restriction digest using SacI and XhoI and ligation with a SacI+XhoI digested mammalian promoter cassette fragment, for example such as FIG. 4B.

Figure 5:
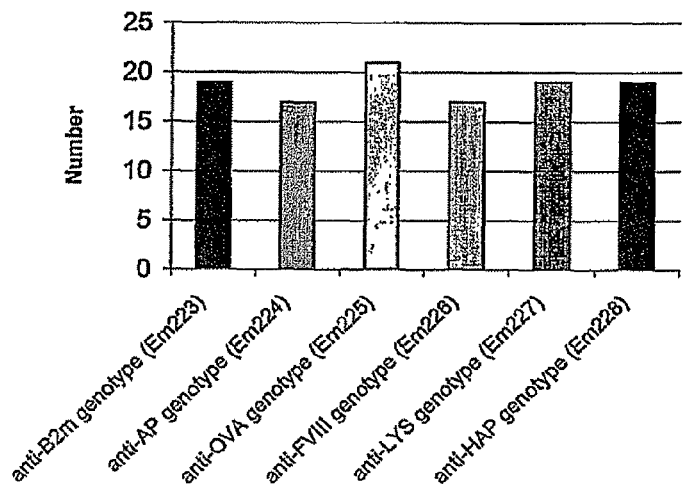

FIG. 5: Histogram showing the genotype distribution in TG1 cells transformed with Plasmid Preparation 1. Em 223-228 refer to vectors with bacterial promoters encoding anti-$β_2$-microglobulin (anti-B2M), anti-alkaline phosphate (anti-AP), anti-ovalbumin (anti-OVA), anti-Factor VIII (anti-FVIII), anti-lysozyme (anti-LYS), anti-haptoglobin (anti-HAP), respectively. Em223-228 are vectors of the pSymvc10-type. The number of individual genotypes resembled by the fragment pattern determined by RFLP corresponds to the number of individual colonies among the total number of picked colonies.

Figure 6:
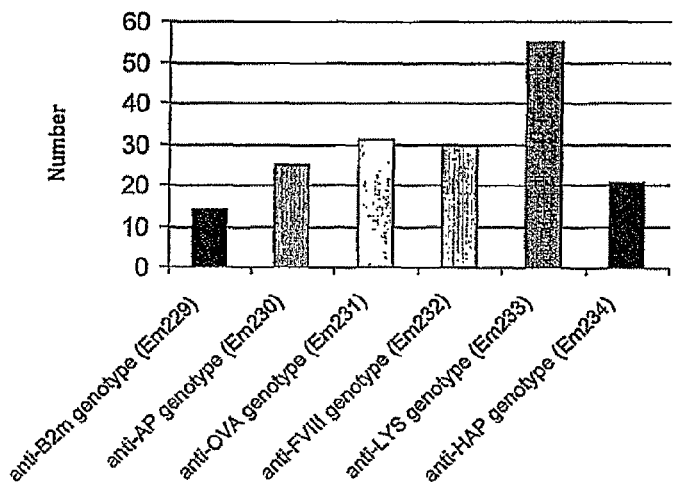

FIG. 6: Histogram showing the genotype distribution in TG1 cells transformed with Plasmid Preparation 2. Em 229-234 refer to vectors with mammalian promoters (CMV/MPSV) encoding anti-$β_2$-microglobulin (anti-B2M), anti-alkaline phosphate (anti-AP), anti-ovalbumin (anti-OVA), anti-Factor VIII (anti-FVIII), anti-lysozyme (anti-LYS), anti-haptoglobin (anti-HAP), respectively. Em 229-234 are vectors of the pSymvc12-type. The number of clones represents the number of clones observed that resemble the sequence pattern determined by RFLP of that Em-type (a complete sequence analysis has not been carried out).

Figure 7:
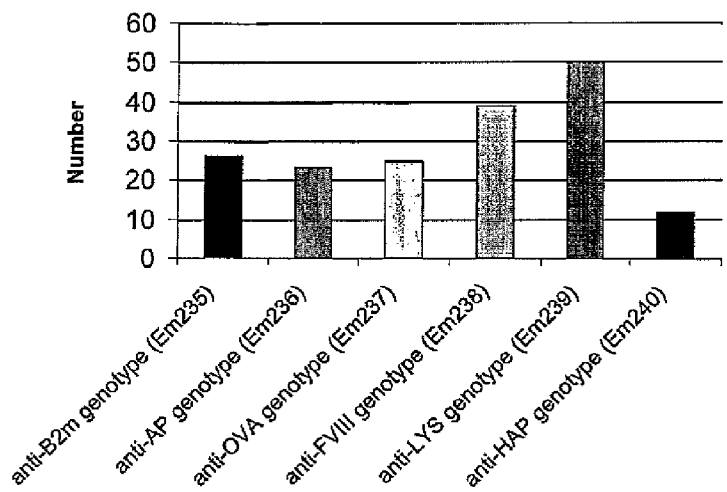

FIG. 7: Histogram showing the genotype distribution in TG1 cells transformed with Plasmid Preparation 3. Em 235-240 refer to a mouse IgG1 mammalian expression vector (including a rabbit β-globin poly A signal) and encoding anti-$β_2$-microglobulin (anti-B2M), anti-alkaline phosphate (anti-AP), anti-ovalbumin (anti-OVA), anti-Factor VIII (anti-FVII), anti-lysozyme (anti-LYS), anti-haptoglobin (anti-HAP), respectively. Em235-240 are vectors of the pSymvc21-type. The number of clones represents the number of clones observed that resemble the sequence pattern determined by RFLP of that Em-type (a complete sequence analysis has not been carried out).

Figure 8:
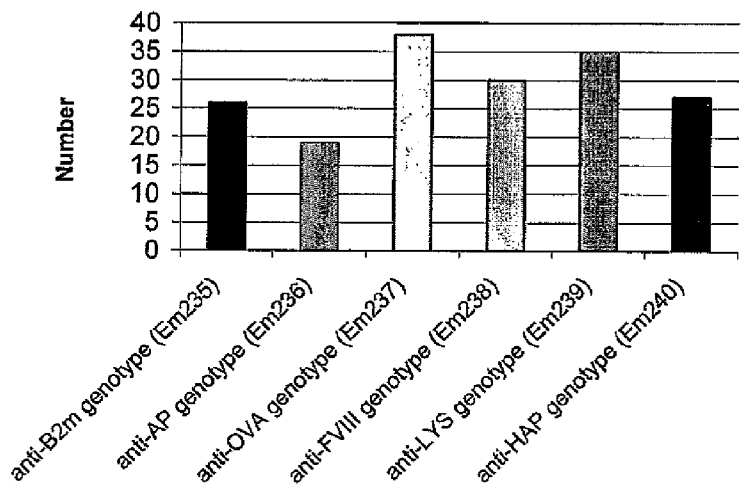

FIG. 8: Histogram showing the genotype distribution in TG1 cells transformed with double digestion/ligation Plasmid Preparation (mass transfer into the mammalian expression vector without DNA amplification in E. coli after Plasmid Preparation 1 step).

Figure 9A:
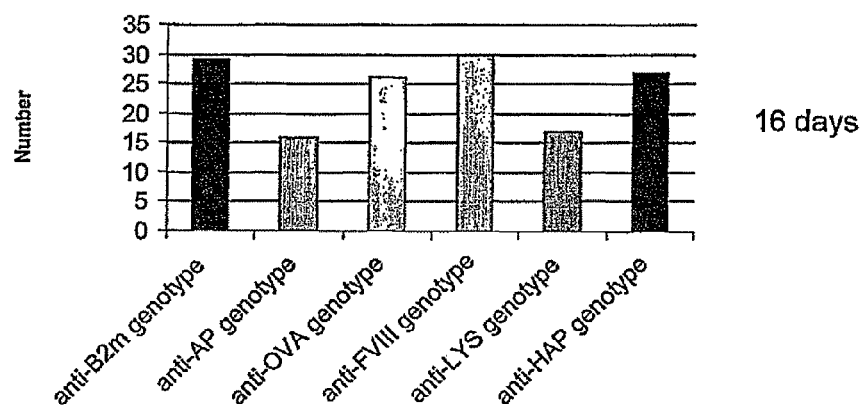
Figure 9B:
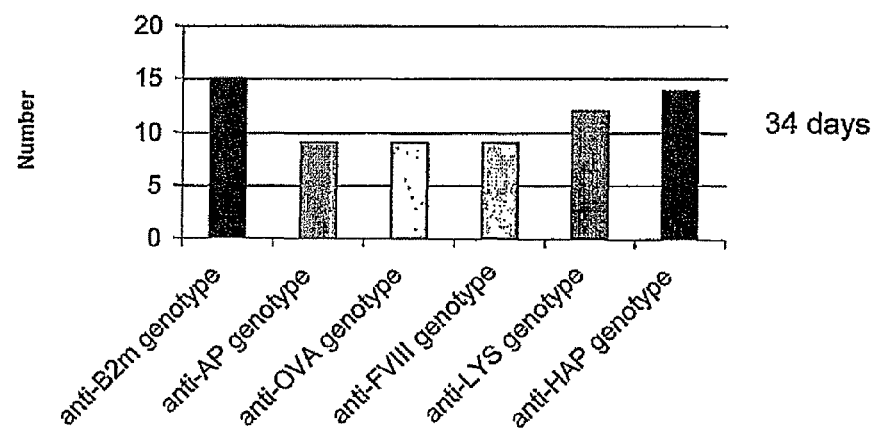

FIG. 9: Histograms showing the genotype distribution in CHO-Flp-In cells transfected with a mixture of mammalian expression vectors encoding the six genes of interest at A) day 16 and B) day 34 post-transfection.

Figure 10:
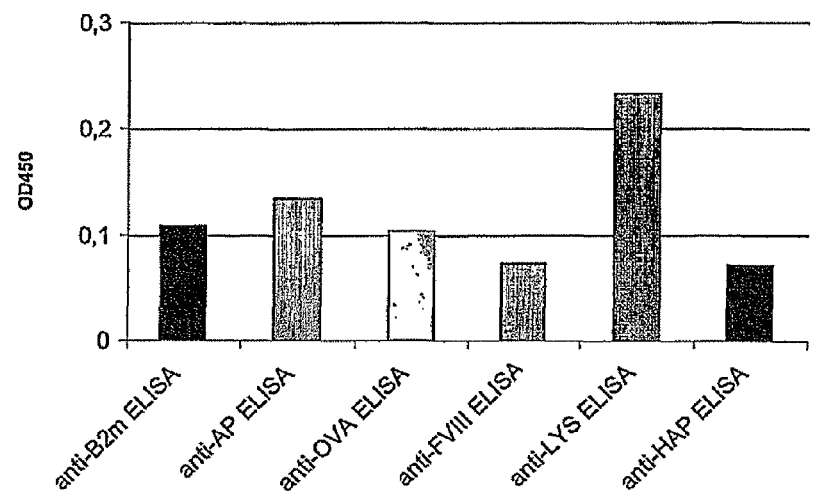

FIG. 10: Antigen-specific ELISA of supernatants derived from CHO-Flp-In cells 34 days after bulk transfection with a mixture of expression vectors encoding the six genes of interest.

Figure 11:
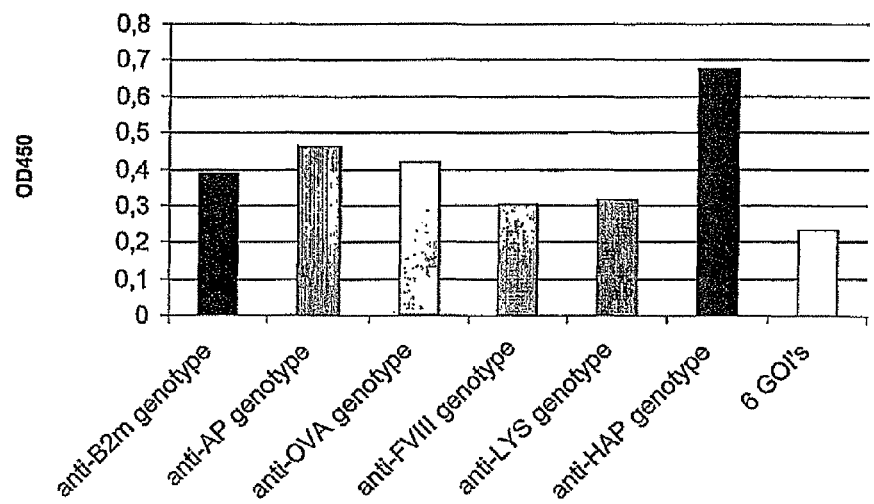

FIG. 11: Anti-kappa coat ELISA of supernatants derived from pools of CHO-Flp-In cells 34 days after transfection either with a single expression vector encoding one gene of interest or a mixture of expression vectors encoding the six genes of interest.

Figure 12:
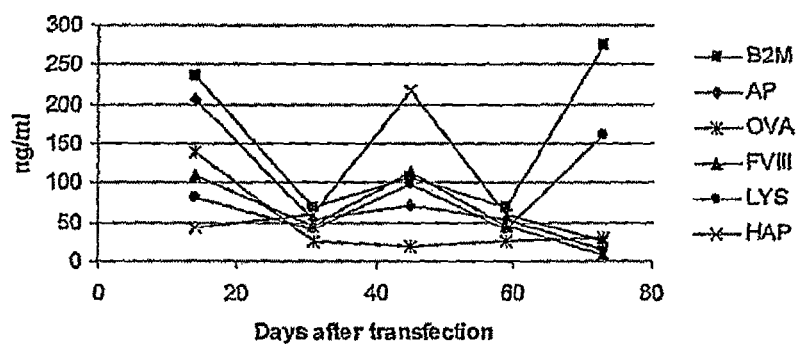
Figure 12:
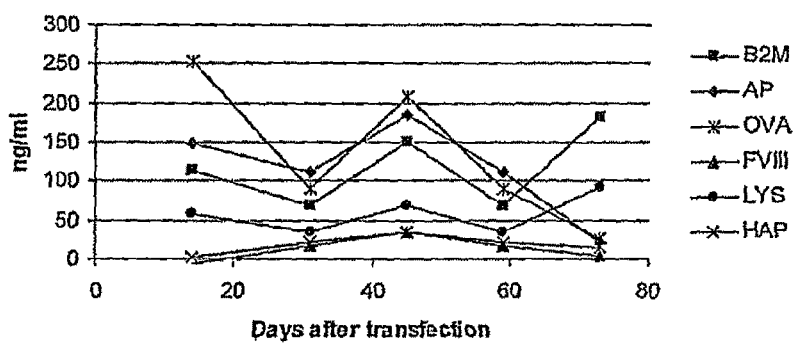
Figure 12:
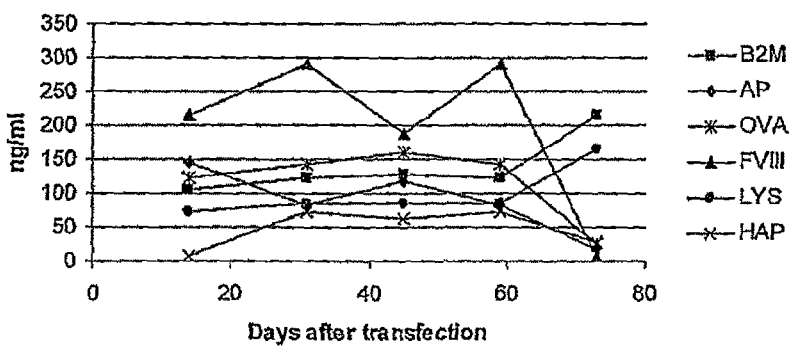

FIG. 12: Quantitative antigen-specific ELISA of supernatants derived from CHO Flp-In clone 019 at day 17, 31, 45, 59 and 73 after bulk transfection with a mixture of expression vectors encoding the six genes of interest. A, S, and C represent three different transfection experiments.

Figure 13:
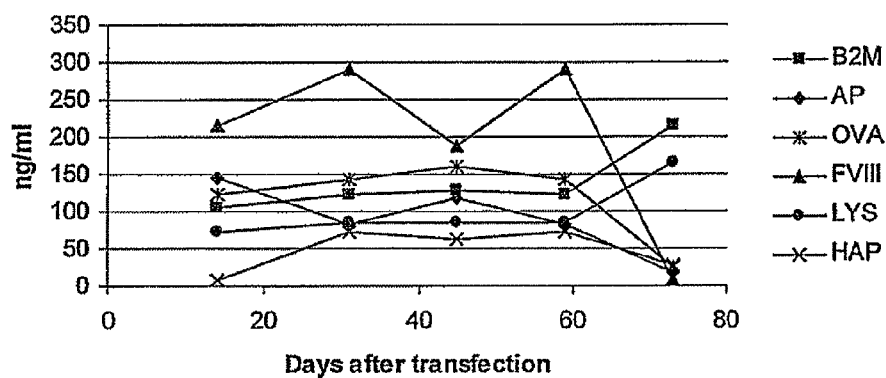

FIG. 13: Antigen-specific ELISA of supernatants derived from CHO Flp-In cell cultures at day 8, 17, 30, 45, 57, 72 and 85 after mixing CHO Flp-In cell lines expressing individual members of the mini six library. Results shown as mean±SD of three Independent experiments.

DETAILED DESCRIPTION OF THE INVENTION

The Recombinant Polyclonal Protein Expression System

The present invention provides methods for the consistent manufacturing of recombinant polyclonal proteins that are preferably selected from the immunoglobulin superfamily, a family of proteins with immunoglobulin-like domains. Most of the members are involved in cell surface recognition events. Sequence homology suggests that antibodies, T cell receptors, MHC molecules, some cell adhesion molecules and cytokines receptors share close homology. Especially members of this family that contain variable regions are suitable for the generation of recombinant polyclonal proteins according to the present invention. Such members include antibodies, membrane bound antibodies (B cell receptors), Fab fragments, Fv fragments, single chain Fv (scFv) fragments, T cell Receptors (TcRs), soluble TcRs, TcR variable domain fragments, TcR variable domain fragments linked by a polypeptide linker or other antibody or TcR derived fragments. In particular, it is contemplated that the present invention will open up the possibility for large-scale manufacturing and production of a new class of therapeutics comprising recombinant therapeutic polyclonal antibodies or TcRs.

One of the major advantages of the manufacturing method of the present invention is that all the members constituting the recombinant polyclonal protein can be produced in between one and approximately 10 bioreactors or equivalents thereof. Further, the recombinant polyclonal protein composition can be purified from the reactor as a single preparation without having to separate the individual members constituting the recombinant polyclonal protein during the process. In contrast, if one wanted to mimic a recombinant polyclonal antibody composition by mixing purified monoclonal antibodies (as for example proposed in WO 91/16074) it would require the separate manufacturing in a bioreactor, of each antibody to be included in the composition and most likely the antibodies would be purified individually as well. Such a production of a monoclonal mixture would be very costly, and time and space consuming compared to the method of producing recombinant polyclonal antibody or other polyclonal proteins as described herein. Thus, the method as described in WO 91/16074 would naturally result in a practical limit to the number of monoclonal antibodies that could be included in such a mixture, most likely below 10, whereas the technology as described herein generally can produce a polyclonal antibody with as many individual members as desired.

In order to obtain predictable expression of a recombinant polyclonal protein from a recombinant polyclonal manufacturing cell line, the regulatory properties of the genomic integration site should be reasonably well understood.

Conventional transfection and recombinant protein expression techniques using random integration are undesirable for the production of a recombinant polyclonal protein, since the random nature of the process will cause the number and positions of the integrated nucleic acid sequences to vary from cell to cell. Thus, if recombinant polygonal protein is produced by such traditional protocols, it is likely to result in a heterogeneous cell culture with variable expression rates of individual members of the polyclonal protein, and genetic instability due to positional effects of the integrated DNA. This will most likely result in a biased expression of the members constituting the polyclonal protein.

Introduction into a predefined genomic site is therefore desirable, this can in principle be achieved by homologous recombination. However, owing to the dominance of illegitimate recombination events, homologous recombination is very inefficient.

Moreover, where the polyclonal protein is an antibody or T cell receptor (TcR), another problem arises with the use of conventional transfection protocols resulting in random integration. Antibodies and TcRs are encoded from pairs of independent gene segments, the light and heavy chain encoding sequences for antibodies and the alpha and beta chain or delta and gamma encoding sequences for TcRs. The polypeptide products from these gene segments become covalently linked during intracellular processing of the antibody molecule or TcR. Conventional transfection technology resulting in random integration leads to the introduction of several copies of different heavy and light chains or alpha and beta chains in the same cell, which results in random combinations of heavy and light chains, so-called $V_H$-$V_L$ chain scrambling or alpha-beta chain scrambling. Consequently, this deteriorates the performance of the expressed antibodies or TcRs causing loss of affinity and/or specificity, the possible occurrence of new specificities and/or reduced specific activity.

To circumvent these problems the expression system of the present invention uses site-specific integration into the genome of the individual host cells The system of the present invention ensures that a library of vectors of interest comprising the variant nucleic acid sequences of interest can be inserted into a pre-characterized chromosomal location by a recombinase-mediated cassette exchange procedure, thereby generating a cell line, wherein the individual cells expresses a single distinct member of the recombinant polyclonal protein of interest. As described below, multiple integrations might occur in some of the cells constituting the recombinant polyclonal manufacturing cell line. This, however, is not considered to pose a problem as long as a majority of the individual cells express a single distinct member of the recombinant polyclonal protein.

Recombinases such as Cre, Flp, beta-recombinase, Gln, Pln, PlnB, PlnD, R/RS, lambda integrase, or phage φC31 integrase can be used. Suitable recombinases for integration into the chromosomal location can be provided either (i) by expression from the cell's own genome into which said nucleic acid sequence is introduced, (ii) by being operatively encoded by the nucleic acid sequence inserted into the cell, (iii) through expression from a second nucleic acid molecule, or (iv) as a protein. In a preferred embodiment, the variant nucleic acid sequence contained in the vector of interest is integrated into a locus that mediates high-level transcription and expression of the nucleic acid sequence of interest, a so-called "hot spot".

The host cell line used is preferably a mammalian cell line comprising those typically used for biopharmaceutical protein expression, e.g., CHO cells, COS cells, BHK cells, myeloma cells (e.g., Sp2/0 cells, NS0), YB2/0, NIH 3T3, and immortalized human cells, such as HeLa cells, HEK 293 cells, or PER.C6. In the present invention CHO cells were used. However, a person of ordinary skill in the art would easily be able to substitute CHO cells with other mammalian cells as described, or even utilize other types of cells, including plant cells, yeast cells, insect cells, fungi and bacteria. Thus the choice of cell type is not intended to be limiting to the invention. In a preferred embodiment, mammalian cells containing a pre-characterized hot spot, mediating high expression levels of the recombinant polyclonal protein of interest are used for the manufacture.

In a further embodiment of the present invention, variant nucleic acid sequences of interest are integrated in a site-specific manner utilizing the same chromosomal integration site in the host cells. Such incorporation into a single specific site minimizes positional effects otherwise seen with random integration or integration into multiple sites in a genome. Especially, when expressing polyclonal proteins composed of more than one polypeptide chain it is further relevant to have a single site, into which the site-specific integration occurs into the genome. This is due to the fact that if a single cell expresses more than one integrant, scrambling among subunits is likely to occur.

In a site-specific integration system, the individual host cells are expressing the same overall protein structure apart from the differences observed in the variable region of the recombinant polyclonal protein of interest, e.g., the antigen-binding region of antibodies or TcRs. Therefore, a majority of cells within such a pool of cells should display similar characteristics with respect to productivity and genetic stability and hence this technology offers the possibility of a controlled production of a recombinant polyclonal protein, e.g., a recombinant polyclonal antibody or TcRs.

The recombinant polyclonal protein of the present invention is intended to cover a protein composition comprising different, but homologous protein molecules, which are naturally variable, meaning that, in preferred embodiments, the library of variant nucleic acids comprises a naturally occurring diversity. Thus, each protein molecule is homologous to the other molecules of the composition, but also contains one or more stretches of variable polypeptide sequence, which is/are characterized by differences in the amino acid sequence between the individual members of the polyclonal protein. The differences in the amino acid sequence(s) that constitute the variable polypeptide sequence might be as little as one amino acid. Preferably the differences in the amino acid sequence constitute more than one amino acid.

Usually, the natural variability of a polyclonal antibody or TcR is considered to be located in the so-called variable regions or V-regions of the polypeptide chains.

In one aspect of the present invention individual members in a polyclonal protein comprise variable regions that are approximately between 80 and 120 amino acids long. The variable regions might contain hyper-variable domains, e.g. complementarity determining regions (CDR).

In naturally occurring TcRs there are four CDRs in each variable region. In natural occurring antibodies there are three CDRs in the heavy chain and three CDRs in the light chain.

In an additional aspect of the present invention the variable regions of the individual members of a polyclonal protein contain at least one hyper-variable domain that is between 1 and 26 amino acids long, preferably between 4 and 16 amino acids long. This hyper-variable domain can correspond to a CDR3 region. For antibodies each variable region preferably constitute three hyper-variable domains. These can correspond to CDR1, CDR2 and CDR3. For TcRs each variable region preferably constitutes four hyper-variable domains. These can correspond to CDR1, CDR2, CDR3 and CDR4. The hyper-variable domains might alone constitute the variable sequences within a variable region of a recombinant polyclonal protein of the present invention.

In the context of the present invention, variability in the polypeptide sequence (the polyclonality) can also be understood to describe differences between the individual antibody molecules residing in so-called constant regions or C regions of the antibody polypeptide chains, e.g., as in the case of mixtures of antibodies containing two or more different antibody isotypes, such as the human isotypes IgG1, IgG2, IgG3, IgG4, IgA1, and IgA2, or the murine isotypes IgG1, IgG2a, IgG2b, IgG3, and IgA. Thus, a recombinant polyclonal antibody may comprise antibody molecules that are characterized by sequence differences between the Individual antibody molecules in the variable region (V region) or in the constant region (C region) or both.

In order to provide variant nucleic acid sequences that encode proteins that bind a particular antigen, a number of methods known in the art may be utilized. Typically, the invention will benefit from the use of a screening procedure that enables identification and/or isolation of nucleic acids that encode protein that bind a particular antigen. Several of these methods include a so-called biopanning step, known from technologies such as phage display (Kang, A. S. et al. 1991. Proc Natl Acad Sci USA 88, 4363-4366), ribosome display (Schaffitzel, C. et al. 1999. J. Immunol. Methods 231, 119-135), DNA display (Cull, M. G. et al. 1992. Proc Natl Acad Sci USA 89, 1865-1869), RNA-peptide display (Roberts, R. W., Szostak, J. W., 1997. Proc Natl Acad Sci USA 94, 12297-12302), covalent display (WO 98/37186), bacterial surface display (Fuchs, P. et al. 1991. Biotechnology 9, 1369-1372), yeast surface display (Boder, E. T., Wittrup, K. D., 1997. Nat Biotechnol 15, 553-557) and eukaryotic virus display (Grabherr, R., Ernst, W., 2001. Comb. Chem. High Throughput. Screen. 4, 185-192), methods that are all known in the art and all are interesting aids in the practice of the present invention. FACS and magnetic bead sorting are also applicable for enrichment (panning) purposes using labeled antigen. Immunodetection assays such as ELISA (Dreher, M. L. et al. 1991. J. Immunol. Methods 139, 197-205) and ELISPOT (Czerkinsky, C. C. et. al. 1983. J Immunol Methods. 65, 109-21) can also be used either following a biopanning step or alone.

A composition of a recombinant polyclonal protein of interest comprises a defined subset of proteins, which have been defined by a common feature such as the shared binding activity towards a desired target, e.g., in the case of polyclonal antibodies against the desired target antigen. Typically a polyclonal protein composition have at least 3, 4, 5, 10, 20, 50, 100, 1000, $10^4$, $10^5$ or $10^6$ distinct variant members. The number of distinct members needed in the polygonal protein composition will depend on the complexity of the target. In the case of antibodies the complexity of the antigen(s) targeted will influence the number of distinct variant members necessary in the polyclonal antibody composition. With small or not very complex targets, for example a small protein, a polyclonal antibody composition that comprises between 3 to 100 distinct variant members will be sufficient, and it is preferred that the number of variants does not exceed 90, or even 80 or 70. In many instances, the number of distinct variants will not exceed 60 or 50, and it is preferred that the number of variants are in the range between 5 and 40, such as between 5 and 30. Whereas for more complex targets, for example viruses with complex or interchangeable surface proteins, or encompassing several virus subtypes, a polyclonal antibody composition that comprises between 20 to 500 distinct variant members will be sufficient. Very complex targets, where the antigen comprises many different molecules, a polyclonal antibody composition comprising between 50 to 10,000 distinct variant members may be required.

In mammals, there are several known examples of naturally occurring polyclonal proteins either circulating freely in the blood such as antibodies or immunoglobulin molecules or present on cell surfaces such as T cell receptors and B cell receptors. The diversity of these naturally occurring polyclonal proteins are, in some mammals, achieved by genetic recombination of genes encoding variable regions of these proteins. Antibodies are further known to increase their diversity by somatic mutation. The present invention can utilize these natural diversities by isolating the sequences responsible for the diversity (e.g., the variable domains or CDR regions of immunoglobulin molecules or TcRs) and generating a library from them. For proteins encoded from two independent gene segments, e.g. antibody variable heavy chain and variable light chain, TcRα chain and β chain or TcRδ chain and γ chain, each vector in the library will constitute a pair of these variable region encoding sequences. The generation of libraries of pairs of variable region encoding sequences is well known in the art.

Libraries comprising naturally occurring diversities are for example, combinatorial libraries (random pairing of the variable region encoding sequences) as well as cognate pair libraries (pairs of variable region encoding sequences derived from the same cell). Further libraries generated from isolated CDR gene fragments, which are incorporated into an appropriate framework (e.g. Soderlind, E. et al., 2000. Nat. Biotechnol. 18, 852-856), such as an antibody or TcR variable region are applicable with the present invention. The libraries are preferably screened to obtain sub-libraries (libraries of interest) with a desired specificity.

Diversities of proteins can also be made in an artificial way, for example synthetic or by mutation. Mutations can either be random or point mutations of a nucleic acid sequence encoding a single protein, thereby generating a polyclonal population of the single protein. Another example of generating artificial antibody libraries are described in EP 0 859 841, a method which is based on generating a library of variable region frameworks which can be combined with another library of CDRs.

In a preferred embodiment of the invention, the recombinant polyclonal protein is a recombinant polyclonal antibody or antibody fragment.

In another preferred embodiment of the invention, the recombinant polyclonal protein is a recombinant polyclonal TcR or TcR fragment.

In addition to the diversity achieved by the genetic and somatic recombination in the so-called variable regions, there are different isotypes of the immunoglobulins, which are defined by the heavy chain. The main isotypes are IgM, IgG, IgA, IgD, and IgE.

A recombinant polyclonal protein of the present invention can therefore also be constituted of the different isotypes or more preferred of different subclasses. Polyclonality of the immunoglobulins can occur in the constant part or in the variable domain of the immunoglobulin molecule or in both the constant part and the variable domain.

Polyclonality in the so-called constant region, particularly the heavy chain of the antibodies, is of interest with regard to therapeutic application of antibodies. The various immunoglobulin isotypes have different biological functions (summarized in Table 1), which might be desirable to combine when utilizing antibodies for treatment because different isotypes of immunoglobulin may be implicated in different aspects of natural immune responses (Canfield and Morrison 1991. J. Exp. Med. 173, 1483-91; Kumpel et al. 2002. Transfus. Clin. Biol. 9, 45.-53; Stirnadel et al. 2000, Epidemiol. Infect. 124, 153-162).

TABLE I

Biological functions of the human immunoglobulin isotypes

| | Human Immunoglobulin | | | | | | | | |
|---|---|---|---|---|---|---|---|---|---|
| | $IgG_1$ | $IgG_2$ | $IgG_3$ | $IgG_4$ | $IgA_1$ | $IgA_2$ | IgM | IgD | IgE |
| Classical complement activation | +++ | ++ | ++++ | + | − | − | ++++ | − | − |
| Alternate complement activation | + | + | + | +++ | + | − | − | + | − |
| Placental transfer | + | ++ | + | ++ | − | − | − | − | − |
| Bacterial lysis | + | + | + | + | +++ | +++ | + | ? | ? |
| Macrophage/other phagocytes binding | + | − | + | + | + | + | − | − | − |
| Mast cell/basophils binding | − | − | − | − | − | − | − | − | − |
| Staphylococcal Protein A reactivity | + | + | − | + | − | − | − | − | − |

A further embodiment of the present invention is a recombinant polyclonal manufacturing cell line, comprising a collection of cells transfected with a library of variant nucleic acid sequences, wherein each cell in the collection is transfected with and capable of expressing one member of the library, which encodes a distinct member of a polyclonal protein that binds a particular antigen and which is located at the same single site in the genome of individual cells in said collection, wherein said nucleic acid sequence is not naturally associated with said cell in the collection.

In an additional embodiment of the above embodiment the variant nucleic acid sequences encoding the polyclonal protein (preferably from the immunoglobulin superfamily) are all derived from naturally occurring sequences, for example isolated from a donor.

Compositions of cells that contain variant nucleic acids located at a single specific site in the genome within each cell has been described in WO 02/44361. This document discloses the use of the cells to identify molecules having desirable properties, but the reference does not deal with the provision of a production system or with the provision of polyclonal protein characterized by a specific binding to an antigen
Clonal Diversity One of the characteristics of a polyclonal protein is that it is constituted by a number of individual protein molecules where each protein molecule is homologous to the other molecules of the polyclonal protein but also has a variability that is characterized by differences in the amino acid sequence between the individual members of the polyclonal protein. Preferably, the differences are confined to distinct areas of the overall structure of the polyclonal protein. Such areas are for example the variable region of an antibody or TcR and possibly further confined to the CDR regions in these areas. This variability can also be described as a diversity, which can be identified both on the nucleic acid level as well as on the protein functional level, e.g., specificity and affinity differences towards a target.

Clonal diversity of the cell line may be analyzed by RFLP (or sequencing of (RT)-PCR products) on isolated clones from a pool of cells expressing a recombinant polyclonal protein. The diversity can also be analyzed by functional tests (e.g., ELISA) on the recombinant polyclonal protein produced by the cell line.

Clonal bias (i.e., a gradual change in the content of the individual antibodies constituting the polyclonal antibody), if it exists, can be estimated by comparing the clonal diversity of the initial library, used for transfection, with the diversity found in the pool of cells (cell line) expressing the recombinant polyclonal protein.

Clonal diversity of a polyclonal protein expressed from a cell line can be assessed as the target coverage by the polyclonal protein. In this case sufficient diversity is considered to be acquired when approximately 25-100% of the desired target molecules are bound by the polyclonal protein. For example in the case of a polyclonal antibody, the binding of antibody to at least 25% of the non-identical epitopes on the surface of a target antigen provides a sufficient diversity in the composition. Preferably, clonal diversity by target coverage is at least 50%, and even more preferable at least 75%. For antibodies such a target coverage could for example be assessed by epitope mapping.

Alternatively clonal diversity can be assessed as the distribution of individual members of the polyclonal composition. This distribution can be assessed as the total number of different individual members in the final polyclonal protein composition compared to the number of different encoding sequences originally introduced into the cell line during transfection. In this case sufficient diversity is considered to be acquired when at least 50% of the encoding sequences originally used in the transfection can be identified as different individual members of the final polyclonal proteins and preferably at least 75%.

The distribution of individual members of the polyclonal composition can also be assessed with respect to the mutual distribution among the individual members. In this case sufficient clonal diversity is considered to be acquired if no single member of the composition constitutes more than 75% of the total number of individual members in the final polyclonal protein composition. Preferably, no individual member exceeds more that 50%, even more preferred 25% and most preferred 10% of the total number of individual members in the final polyclonal composition. The assessment of clonal diversity based on the distribution of the individual members in the polyclonal composition can be performed by RFLP analysis, sequence analysis and protein analysis such as the approaches described later on for characterization of a polyclonal composition.

Clonal diversity may be reduced as a result of clonal bias which can arise a) during the cloning process, b) as a result of variations in cellular proliferation, or c) through scrambling of multiple integrants. If such biases arise, each of these sources of a toss of clonal diversity is easily remedied by minor modifications to the methods as described herein.

In order to limit bias introduced by cloning of the variable domains into the appropriate vectors, the transfer of the genes of interest from one vector to another may be designed in such a way that cloning bias is limited. Mass transfer techniques and a careful selection of the E. coli strain used for amplification can reduce the cloning bias. Another possibility is to perform an individual transfer of each polynucleotide encoding an individual member of the polyclonal protein, between vectors of the invention.

It is possible that variations in cellular proliferation rates of the individual cells in the cell line could, over a prolonged period of time, introduce a bias into the recombinant polyclonal protein expression, increasing or reducing the presence of some members of the recombinant polyclonal protein expressed by the cell line. One reason for such variations in proliferation rates could be that the population of cells constituting the starting cell line used for the initial transfection is heterogeneous. It is known that individual cells in a cell line develop differently over a prolonged period of time. To ensure a more homogeneous starting material, sub-cloning of the cell line prior to transfection with the library of interest may be performed using a limiting dilution of the cell line down to the single cell level and growing each single cell to a new population of cells (so-called cellular sub-cloning by limiting dilution). One or more of these populations of cells are then selected as starting material based on their proliferation and expression properties.

Further, the selection pressure used to ensure that only cells that have received site-specific integrants will survive, might affect proliferation rates of individual cells within a polyclonal cell line. This might be due to the favoring of cells that undergo certain genetic changes in order to adapt to the selection pressure. Thus, the choice of selection marker might also influence proliferation rate-induced bias. If this occurs, different selection markers should be tested. In cases where selection is based on a substance that is toxic to the cells, the optimal concentration should be tested carefully, as well as whether selection is needed throughout the entire production period or only in the initial phase.

An additional approach to ensure a well defined cell population is to use fluorescence activated cell sorting (FACS) after the transfection and selection procedures. Fluorescence labeled antibodies can be used to enrich for highly productive cells derived from a pool of cells transfected with IgG constructs (Brezinsky et al. J. 2003. Immunol Methods 277, 141-155). This method can also be used to sort cells expressing similar levels of immunoglobulin, thereby creating a homogenous cell population with respect to productivity. Likewise, by using labeling with the fluorescent dye 5,6-carboxylfluorescein diacetate succinimidyl ester (CFSE) cells showing similar proliferation rates can be selected by FACS methods.

Even if a proliferation rate-induced bias does develop, the loss or over-representation of individual members might not necessarily be critical, depending on the diversity requirements of the final recombinant polyclonal protein product and the stability of the diversity over time.

In site-specific single integrants, the cells will only differ in the sequence of the variable regions of the antibodies to be expressed. Therefore, the different cellular effects imposed by variation in integration site and gene regulatory elements are eliminated and have minimal effects on the cellular proliferation rate. Neither scrambling nor multiple integrations is likely to cause problems in the proliferation rate of the manufacturing cell line, since these are rare events. Random integrations generally occur with an efficiency of approximately $10^{-5}$, whereas site-specific integration occurs with an efficiency of approximately $10^{-3}$. If multiple integrations should unexpectedly pose a problem, an alternative is to repeat the transfection with the library of vectors of interest, because the likelihood that the event will reoccur is very small, as described above. Additional alternatives are described in Example 3 below.

Another method of controlling unwanted clonal bias is to perform the transfection with the entire library of vectors of interest in several sub-pools or to split the cell pool at an early time point after transfection into sub-pools. At this point, the bias should not have become significant and it should be statistically possible to acquire sub-pools that lack clones with an unwanted proliferation advantage. The resulting exclusion of unwanted clones has to be in agreement with the requirements of diversity in the final recombinant polygonal protein product. Considering statistics, bulk transfection of a large number of cells also constitutes a way to circumvent an undesired clonal bias. In this approach, a host cell line is transfected in bulk with the library of variant nucleic acid sequences. Such a library constitutes many copies of each distinct member of the library. These copies should preferably be integrated into a large number of host cells. Preferably at least 100, 1000, 10000 or 100000 individual cells are transfected with copies of distinct members of the library of variant nucleic acid sequences. Thus, if a library of distinct variant nucleic acid sequences is composed of 1000 distinct members which are each integrated into 1000 individual cells, $10^6$ clones containing a sitespecifically integrated GOI should arise from the transfection. In this manner the gausian curve of individual cell doubling rates should influence the general population only in very small degrees. This will increase the probability of keeping the clonal composition constant over time even if a low percentage of the manufacturing cells should exhibit aberrant growth and/or expression properties.

Alternatively, the library of vectors of interest can be split into fractions containing approximately 5 to 50 individual vectors of the library. Preferably, a fraction of the library constitutes 10 to 15 individual vectors. Each fraction is then transfected into an aliquot of cells. The individual aliquots of cells can then be followed for a period of time to see if clonal bias develops in any of them. If this happens such aliquots of cells can be omitted before the collection of cells is reconstituted by pooling the remaining aliquots of cells. Optionally, the aliquots of cells are kept separate throughout production, and the polyclonal antibody composition is assembled by combining the products of each aliquot rather than the aliquots of cells before production. The number of pools that can be handled are expected to be between five to ten to (see the previous description of monoclonal antibodies).

Alternatively, a high throughput method may be implemented in which cells are transfected separately using vectors and cells based on single clones from the initial library of vectors of interest. This may eliminate any possible sequence bias during transfection and integration. Optionally, the single transfectants may be genotyped and a fully diverse pool of cells assembled just prior to production or earlier if appropriate. Alternatively, the individual transfection of a large number of cells, generating many clones with the same distinct member of the library of variant nucleic acid sequences may produce the same statistical advantages described for bulk transfection, when the individually transfected cells are pooled prior to the manufacture of the polyclonal protein.

The Host Cell

A suitable host cell comprises, in a region of its genome, one or more suitable recombination sites, i.e., nucleic acid sequences recognizable by one or more recombinase enzymes. To be able to select for integrants, (i.e., cells having an integrated copy of the nucleic acid sequence of interest in an integration site) the recombination site is operably linked to a first selection gene (e.g., an antibiotic resistance gene) situated 3' to the recombination site. Furthermore, a weak promoter (e.g., a truncated SV40 early promoter) and a transcription start codon may be situated 5' to the recombination site that constitutes an integral part of the resistance marker-coding region. Thus, the transcription start codon initiates the start of transcription of the selection gene in the host cell before transfection with the library of expression vectors encoding the polyclonal protein.

Host cells for site-specific integration as described above can be generated from any cell which can integrate DNA into their chromosomes or retain extra-chromosomal elements such as mini-chromosomes, YACs (Yeast artificial chromosomes), MACs (Mouse artificial chromosomes), or HACs (Human artificial chromosomes). MACs and HACs are described in detail in WO 97/40183, hereby incorporated by reference. Preferably mammalian cells such as CHO cells, COS cells, BHK cells, myeloma cells (e.g., Sp2/0 or NS0 cells), fibroblasts such as NIH 3T3, and immortalized human cells, such as HeLa cells, HEK 293 cells, or PER.C6, are used. However, non-mammalian eukaryotic or prokaryotic cells, such as plant cells, insect cells, yeast cells, fungi, E. coli etc., can also be employed.

In one embodiment of the present invention, the cell line which is to be used as starting material is sub-cloned by performing a so-called limiting dilution of the cell line down to a single cell level, followed by growing each single cell to a new population of cells prior to transfection with the library of vectors of interest. Such sub-cloning can also be performed later in the process of selecting the right cell line, if desired.

The host cells for site-specific integration may be obtained by transfection with a randomly integrating plasmid comprising a weak promoter (e.g., a truncated SV40 early promoter), a transcription start codon, a recombination site situated 3' to the start codon. Preferably, the integrating plasmid also comprises a marker gene coupled to a first selection gene. One example of such an integrating plasmid is the pFRT/LacZeo2 from Invitrogen (Carlsbad, Calif.). The marker gene can be used to evaluate the relative strength of expression at the genomic location used for inserting a nucleic acid sequence of interest. A marker gene, (e.g., beta-galactosidase (LacZ), green fluorescent protein (GFP) or a cell surface marker) can be linked to the first selection gene in a gene fusion or transcriptionally linked by an IRES (internal ribosomal entry site) such that co-expression of the first selection gene and marker gene occurs. The use of a selection gene that establishes a survival pressure on the cells (e.g. drug resistance or nutritional depletion) combined with a marker allowing for evaluation of the relative expression levels from cell line to cell line is an efficient method to ensure high producing cells which maintain the integrated plasmid within the genome. Cells with the recombination sequence inserted at a spot with particularly active transcription will lead to high expression of the marker gene e.g. GFP or LacZ. High expressers can be selected by fluorescence activated cell sorting (FACS) and cloned. At this point it should also be analyzed whether the integrant is a single integrant. This can be performed by real-time PCR and Southern blotting.

Another method for evaluating relative expression levels from cells transfected with an integrating plasmid is to perform an additional integration-excision step on the cells generated as described above. This pool of selected cells are transfected again, with a plasmid encoding a recombinase corresponding to the recombination site of the integrating plasmid and a second plasmid containing a second selection marker without a start codon, the coding region of which is preceded by a recombination sequence likewise corresponding to the first integrating plasmid. This second plasmid also contains the coding sequence for a fluorescent marker protein (e.g., GFP (or equivalent fluorescent proteins) driven by a mammalian promoter. The recombinase mediates integration of this plasmid into the host cell genome where a similar recombination sequence previously has been inserted by the integrating plasmid. Cells with the recombination sequence inserted at a spot with particularly active transcription will lead to high expression of the fluorescent protein. High expressers are selected by fluorescence activated cell sorting (FACS) and cloned. Clones with consistently high expression and containing one copy of the inserted plasmid are transfected with the recombinase and selected by the first selection marker, identifying cells where the second plasmid sequence has been removed by the recombinase, making the first selection marker work again. These cells still contain the first recombination sequencer inserted at a transcriptional hotspot and can now be used for the expression of genes of interest.

Cell lines, which achieve high expression of the marker gene upon integration of a single copy of the plasmid, are used for transfection with the gene of interest. The recombination site in the host cell is preferably located in a gene or region of particularly active expression, i.e., in a so-called hot spot.

The Vector for Site-Specific Integration

A suitable vector comprises a suitable recombination site linked to a suitable selection gene different from the selection gene used for construction of the host cell. Suitable selection genes for use in mammalian cell expression include, but are not limited to, genes enabling for nutritional selection, such as the thymidine kinase gene (TK), glutamine synthetase gene (GS), tryptophan synthase gene (trpB) or histidinol dehydrogenese gene (hisD). Further, selection markers are antimetabolite resistance genes conferring drug resistance, such as the dihydrofolate reductase gene (dhfr) which can be selected for with hypoxanthine and thymidine deficient medium and further selected for with methotrexate, the xanthine-guanine phosphoribosyltransferase gene (gpt), which can be selected for with mycophenolic acid, the neomycin phosphotransferase gene (neo) which can be selected for with G418 in eukaryotic cell and neomycin or kanamycin in prokaryotic cells, the hygromycin B phosphotransferase (hyg, hph, hpt) gene which can be selected for with hygromycin, the puromycin N-acetyltransferase gene (pac) which can be selected with puromycin or the Blasticidin S deaminase gene (Bsd) which can be selected with blasticidin. Finally, genes encoding proteins that enables sorting e.g. by flow cytometry can also be used as selection markers, such as green fluorescent protein (GFP), the nerve growth factor receptor (NGFR) or other membrane proteins, or beta-galactosidase (LacZ).

In one aspect of the present invention, the selectable gene is neither preceded by a promoter nor equipped with a translation initiating codon. The promoter and ATG codon is provided at the selected site-specific recombination site. If this vector is integrated at a location other than the selected recombination site in the genome of the host cell, no expression of this second selection gene can occur due to lack of promoter and initiation codon. If integration occurs at the selected recombination site in the genome of the host cell, the second selection gene is expressed and expression of the first selection gene is lost.

Integration may e.g., be carried out using a so-called FRT site (5'-gaagttcctattccgaagttcctattctctagaaagtataggaacttc-3' (SEQ ID NO 1) and variants thereof) in the genome and on the vector for site-specific integration together with the Flp recombinase or mutants thereof from *Saccharomyces cerevisiae*. However, other recombinase systems may equally well be used, including those of Cre recombinase and a variety of lox sites such as loxP from bacteriophage P1 or variants or mutants thereof, e.g., lox66, lox71, lox76, lox75, lox43, lox44 and lox511 (C. Gorman and C. Bullock, Curr. Opinion in Biotechnology 2000, 11: 455-460) or by using phage integrase φC31 or lambda integrase, which carries out recombination between the attP site and the attb site (A. C. Groth et al. PNAS 2000, 97: 5995-6000). Further recombinase systems that could be utilized in the present invention are, but are not limited to, the β-recombinase-six system from bacterial plasmid pSM19035, the Gln-glx system from bacteriophage Mu or the R-RS system from *Zygosaccharomyces rouxii*.

A further variant to the site-specific recombination system is to use non-homologous recombination sites. In such a system, two non-identical recombination sites are introduced into the host genome for the generation of specific target sites. Recombination sites corresponding to those flanking the target site also flank the construct containing the gene of interest. Such a system has been described in WO 99/25854, which is hereby incorporated by reference in its entirety. The use of non-homologous recombination sites was shown to suppress excision of the GOI from the chromosome. The non-identical recombination sites can be composed of any of the recombination sites described above as long as the corresponding recombinases are provided. For example, non-identical recombination sites could consist of a FRT site and a mutant FRT site utilizing a Flp recombinase for integration or a FRT site and a loxP site utilizing Flp and Cre recombinases for the integration.

Further, a system using two different FRT sites has been described in Verhoeyen et al., Hum. Gene Ther. 2001 12, 933-44. In this approach the integrating plasmid is transferred to the host cells by retroviral infection. The plasmid consists of a combination of a reporter gene and a first selection marker gene as well as the retroviral elements required for infection. The retroviral 3'LTR contains two different FRT sites. A non functional second selection marker gene, which lacks a promoter and the translation initiating codon is located 3' to theses sites. During the process of retroviral infection the 3'LTR sequence is copied to the 5'LTR. This results in the flanking of the reporter gene and the first selection marker gene by two different FRT sites on each side. The sequence between the outer FRT sites can be exchanged against a GOI under the control of a strong promoter. The cassette containing the GOI is flanked by the same set of FRT sites. The reaction is catalyzed by the Flp recombinase. In the transfected exchange plasmid an IRES element and a translation initiating codon are located further downstream of the GOI. After replacement of the integrated cassette the non functional selection marker gene located in the 3' LTR sequence outside the FRT sites is activated by the translation initiating codon provided by the GOI constituting cassette. The exchange status can further be enriched if a negative selection marker (e.g. thymidine kinase) is present in the integrating vector.

The integrating vector can also be transferred to the host cells by standard transfection. In this case the integrating cassette is flanked by an FRT at the 5' end and a different FRT'site at the 3' end. The ATG-deficient second resistance marker gene is positioned further downstream of the 3' FRT' site. The exchange for a GOI proceeds as described for the retroviral system.

Another system that prevents excision of the GOI after its site-specific integration into the chromosome is the φC31 integrase, also mentioned above. This system has been described thoroughly in patent applications WO 01/07572 and WO 02/08409, hereby incorporated by reference in their entirety.

In a further aspect of the invention, the vector for site-specific integration of the gene of interest further comprises DNA encoding one member of the recombinant polyclonal protein of interest, optionally preceded by its own mammalian promoter directing expression of the protein. If a member of the recombinant polyclonal protein of interest comprises more than one protein chain, e.g., if the member is an antibody or T cell receptor, the DNA encoding the chains of the protein can be preceded by their own mammalian promoter directing high levels of expression (bi-directional or uni-directional, see FIGS. 1 and 2, respectively) of each of the chains. In a bi-directional expression a head-to-head promoter configuration in the expression vector can be used and for a uni-directional expression two promoters or one promoter combined with e.g., an IRES sequence can be used for expression. Suitable head-to-head promoter configurations are for example, but not limited to, the AdMLP promoter together with the mouse metallothionein-1 promoter in both orientations, the AdMLP promoter together with the elongation factor-1 promoter in both orientations or the CMV promoter together with the MPSV promoter in both orientations.

A nucleic acid sequence encoding a functional leader sequence can be included in the expression vector to direct the gene product to the endoplasmic reticulum or a specific location within the cell such as an organelle. A strong polyadenylation signal can be situated 3' of the protein-encoding DNA sequence. The polyadenylation signal ensures termination and polyadenylation of the nascent RNA transcript and is correlated with message stability. The DNA encoding a member of the recombinant polyclonal protein of interest can, for example, encode both the heavy and light chains of an antibody or antibody fragments, each gene sequence optionally being preceded by their own mammalian promoter elements and/or followed by strong poly A signals directing high level expression of each of the two chains.

The expression vector for site-specific integration can carry additional transcriptional regulatory elements, such as enhancers or UCOE (ubiquitous chromatin opening elements) for increased expression at the site of integration. Enhancers are nucleic acid sequences that interact specifically with cellular proteins involved in transcription. The UCOE opens chromatin or maintains chromatin in an open state and facilitates reproducible expression of an operably-linked gene (described in more detail in WO 00/05393, hereby incorporated by reference in its entirety). When one or more of the regulatory elements described in the above are integrated into the chromosome of a host cell they are termed heterologous regulatory elements.

Establishing an Expression System for High-Level Expression of Proteins

Methods for introducing a nucleic acid sequence into a cell are known in the art. These methods typically include the use of a DNA vector to introduce the sequence of interest into the cell, the genome or on extra-chromosomal element. Transfection of cells may be accomplished by a number of methods known to those skilled in the art, including calcium phosphate precipitation, electroporation, microinjection, liposome fusion, RBC ghost fusion, protoplast fusion, and the like.

For the transfection of a host cell line, a library of vectors of interest, wherein each vector comprises only one copy of a nucleic acid sequence encoding one member of a recombinant polyclonal protein of interest, is used. This library of expression vectors of interest collectively encodes the recombinant polyclonal protein of interest. Suitable vectors for site-specific integration was described in the previous section. The individual vectors constituting the library of variant nucleic acid sequences of interest can either be mixed together into a single composition, or the individual vectors encoding each library member can be kept in separate compositions or in mixtures of approximately 5 to 50 individual vectors of the library in a composition.

Figure 3:
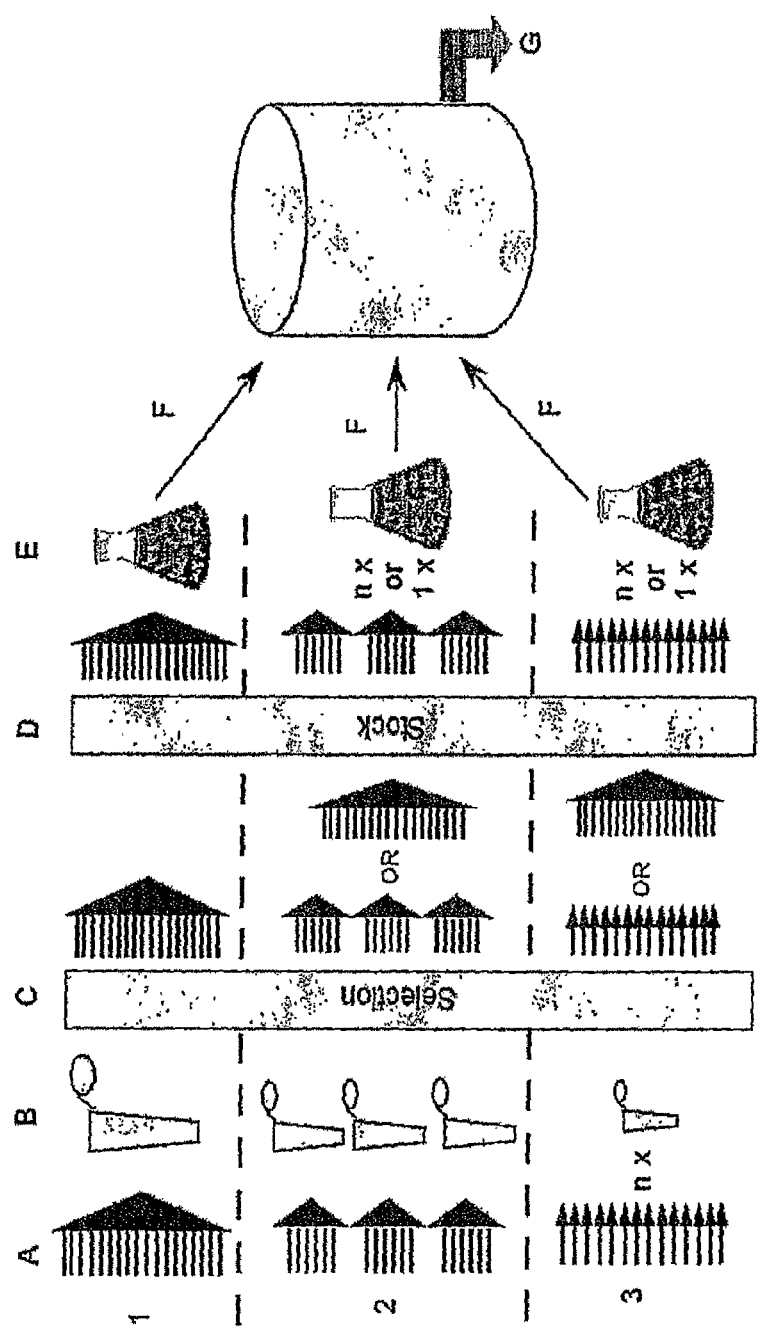
FIG. 3: Flow chart outlining the generation of a recombinant polyclonal manufacturing cell line and the production of a recombinant polyclonal protein. 1) Illustrates a bulk transfection strategy; 2) illustrates a semi-bulk transfection strategy and 3) illustrates an individual transfection strategy. A) Illustrates the library of vectors (horizontal lines), the arrowheads illustrate the grouping of the vectors. In strategy 1 the vectors are grouped in bulk, in strategy 2 they are grouped in smaller fractions (semi-bulk), whereas in strategy 3 they are kept separate from each other (individual). B) Illustrates the transfection, where the number of tubes depend on the grouping of the vectors constituting the library. C) Illustrates selection of cells that site-specifically have integrated a GOI into the host cell genome, D) Illustrates the generation of a polyclonal GOI library stock, where the selected cells constituting the integrated library are stored in a freezer. It is optional to bank individual clones or pool the clones, E) Illustrates the beginning of the manufacturing phase, where clones from the stock are thawed (either individually, from smaller fractions or from a pool) and adapted to growth in suspension. Adaptation to serum free media can be performed after the selection stage or at this stage. F) Illustrates the stage in the production where the polyclonal cell line is propagated for seeding of a larger bioreactor (intermediate seeding steps are an option although not illustrated). In strategy 2 and 3, this is the stage where the polyclonal cell clone stock no longer is kept as individual clones or semi-bulk fractions, but pooled into a collection of cells, forming a recombinant polyclonal manufacturing cell line. G) Illustrates the final production obtained from the bioreactor manufacturing. Following the production phase, the polyclonal protein composition is harvested for purification and characterization of the product.

The generation of a recombinant polyclonal manufacturing cell line and the production of a recombinant polyclonal protein from such a cell line can be obtained by several different transfection and manufacturing strategies. These strategies are outlined in FIG. 3.

One way, is to use a library of vectors mixed together into a single composition for the transfection of a host cell line. This method is termed bulk transfection or transfection in bulk. Generally the vector and host cell design previously described will ensure that a polyclonal cell line will be obtained upon appropriate selection. In such a cell line a majority of the individual cells have integrated one copy of a nucleic acid molecule, encoding a distinct member of a recombinant polyclonal protein, from a library of nucleic acid sequences of interest into the genome. The single copy of the nucleic acid sequence is integrated into a single specific site of the genome of each cell in the collection of cells, thereby generating a polyclonal cell line comprised of individual cells expressing individual members of the polyclonal protein of interest. A frozen stock of the polyclonal cell line will be generated before initiation of the recombinant polyclonal protein manufacturing.

Another way is to use a library of vectors split into fractions, containing approximately 5 to 50 individual vectors of the library in a composition, for transfection. Preferably, a fraction of the library constitutes 10 to 20 individual vectors. Each composition is then transfected into an aliquot of host cells. This method is termed semi-bulk transfection. The number of aliquots transfected will depend on the size of the library and the number of individual vectors in each fraction. If the library for example constitutes 100 distinct variant members, which are split into fractions containing 20 distinct variant members in a composition, 5 aliquots of host cells would need to be transfected with a library composition constituting a distinct fraction of the original library. The aliquots of host cells are selected for site-specific integration. Preferably, the distinct aliquots are selected separately. However, they can also be pooled before selection. The aliquots can be analyzed for their clonal diversity and only those with sufficient diversity will be used to generate a polyclonal GOI library stock. To obtain the desired polyclonal cell line for manufacturing, the aliquots can be mixed before generating the freezing stock, immediately after they have been retrieved from the stock or after a short proliferation and adaptation time. Optionally, the aliquots of cells are kept separate throughout production, and the polyclonal protein composition is assembled by combining the products of each aliquot rather than the aliquots of cells before production.

A third way, is a high throughput method in which host cells are transfected separately using the individual vectors constituting the library of interest. This method is termed individual transfection. The individually transfected host cells are preferably selected for site-specific integration separately. However, they can also be pooled before selection. The individual cell clones generated upon selection may be analyzed with respect to proliferation time and integration pattern and preferably, those with similar growth rates and a single site-specific integration are used to generate a polyclonal GOI library stock. The individual cell clones can be mixed to obtain the desired polygonal cell line before generating the stock, immediately after they have been retrieved from the stock, or after a short proliferation and adaptation time.

This approach may eliminate any possible residual sequence bias during transfection, integration and selection. Alternatively the individually transfected host cells are mixed before selection is performed, this will enable control of sequence bias due to transfection.

A shared feature in the manufacturing strategies outlined in the above is that all the individual members constituting the recombinant polyclonal protein can be produced in one, or a limited number of bioreactors, with approximately 10 as the maximum. The only difference is the stage at which one chooses to generate the collection of cells that constitutes the recombinant polyclonal manufacturing cell line.

The host cell line to be used for expression and production of a recombinant polyclonal protein of interest has one or more nucleic acid molecule(s) recognizable by a recombinase enzyme(s) (e.g., cells prepared beforehand having an FRT site at a pre-determined location in the genome as described in e.g., U.S. Pat. No. 5,677,177).

The vector for site-specific integration is preferably integrated in a predefined genomic locus that mediates high-level expression, a so called hot spot.

If expression levels need to be increased, gene amplification can be performed using selection for a DHFR gene or a glutamine synthetase (GS) gene. This requires the use of vectors comprising such a selection marker.

For the manufacturing of a polyclonal protein, where each protein member is comprised of more than two polypeptide chains, the combination of the chains might be of importance for the affinity, specificity and activity of the protein they form. This is for example seen for anti-bodies and TcRs. For example, is the combination of antibody variable heavy chain and variable light chain known to affect affinity and specificity of an antibody formed from the chains. Thus, when a library of antibody encoding sequences has been selected for their ability to produce antibodies with affinity to a certain target it is desirable to ensure that the combination of the variable heavy chain and variable light chain in the final product correspond to this. For this reason the polypeptide chains constituting an individual member of the polyclonal protein are placed in the same vector used for integration, thereby ensuring that they will be kept together throughout the process.

The following description is one example of how to obtain a recombinant polyclonal antibody expressing cell liner where scrambling of the chains is minimal if existing at all.

A universal promoter cassette for constitutive expression having two promoters placed in opposite transcriptional direction, such as a head-to-head construction surrounded by the variable heavy chain and the whole of the kappa light chain was constructed, allowing transfer of the whole construct into a vector for site-specific integration said vector comprising a FRT site and a hygromycin resistance gene and the heavy chain constant region. It is contemplated that a promoter cassette for inducible expression can also be used. Furthermore, the promoters can be placed tail-to-tail which will result in transcription in opposite direction or tail-to-head for unidirectional transcription. CHO-Flp-In cells (Invitrogen, Carlsbad, Calif.) which stably express the lacZ-Zeocin fusion gene, were used for the experiment, rendering the cells resistant to the antibiotic Zeocin. The cells were maintained in a medium containing Zeocin. The cells were transfected in bulk with the library of vectors for site-specific integration encoding the polyclonal antibody and a different selection marker (hygromycin phosphotransferase) together with a plasmid expressing the Flp recombinase. An inducible promoter can also be used for control of the expression. After transfection, the cells were cultivated in the presence of hygromycin. Cells that were resistant to hygromycin were subsequently grown in different culture systems, such as conventional small culture flasks, Nunc multilayer cell factories, small high yield bioreactors (MiniPerm, INTEGRA-CEL-Line) and spinner flasks to hollow fiber- and bioreactors. The cells were tested for antibody production using ELISA. Polyclonal cell lines were selected for viability in suspension growth in serum free medium without selection pressure for extended periods. Stocks of cell lines were grown in the presence of hygromycin.

Evaluation of the Preservation of Polyclonality in the Expression System

According to the present invention, it is often important to ensure that the polyclonality in the expression system is not seriously altered during production so that it is possible to stop the production when polyclonality is indeed altered. This is according to the invention done by monitoring the relative expression levels of the variant nucleic acid sequences. The expression levels can for example be monitored at mRNA level using for example RFLP analysis, arrays or real-time PCR, or at the protein level using for example two-dimensional polyacrylamide gel electrophoresis, mass spectrometry or various chromatographic techniques. With these techniques it will be possible to establish a baseline value for a number of all of the individual expression levels and then take out samples from the culture during production in order to gauge whether expression levels have changed (both in total and relatively). In normal practice of the invention, a range of values surrounding the baseline values can be established, and if the relative expression levels are found to be outside the ranges, then production is terminated.

To be able to evaluate the stability and reproducibility of the expression system, vectors encoding six distinct Fab fragments (the mini six library) with reactivity against chicken ovalbumin (OVA), bovine alkaline phosphatase (AP), human $\beta_2$-microglobulin ($\beta_2$m), human haptoglobin (HAP), human Factor VIII (FVIII) and hen egg white lysozyme (LYS) were prepared. The different Fab fragment encoding sequences are not identical and therefore exhibit different RFLP patterns, whereby RFLP can be used for analyzing the genotype composition.

The mini six library was introduced into CHO-Flp-In cells by transfection using an expression vector with a head-to-head promoter cassette. The CHO-Flp-In cells were either transfected in bulk with a mixture of expression vectors of interest encoding the six distinct antibodies resulting in a polyclonal cell line expressing the six antibodies in known combination or the cells were transfected individually with one member of the expression library of interest followed by mixing of the transfected cells, generating a recombinant polyclonal antibody expressing cell line expressing the six antibodies in known combination. In this manner, it was possible to test whether the transfection of the mammalian cells occurs without generating a bias to one or several individual clones of the recombinant polyclonal antibody expressing cell line. Furthermore, it was possible to check for proliferation bias and bias caused by the purification of the polyclonal composition of antibodies.

Establishment of an Anti-Ovalbumin Recombinant Polyclonal Antibody Manufacturing Cell Line Ovalbumin-binding phage clones were selected using phage display and ELISA to identify the relevant clones. Two setups were used for identifying antibodies from the ovalbumin-binding clones, i.e., ELISA plates coated with ovalbumin or a high density screening method (HDS), based on immobilization of ovalbumin on PVDF membranes. In this manner a panel of anti-bodies were obtained, of which some recognize ovalbumin immobilized on the ELISA plate and others recognize ovalbumin immobilized on the PVDF membrane.

Figures 4, 4E:
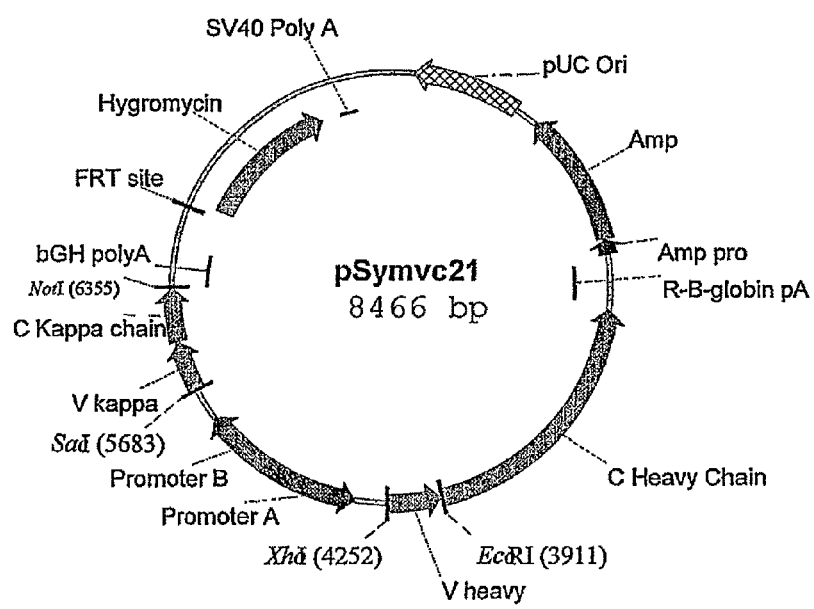

The selected ovalbumin-binding phage clones may have their variable heavy and kappa chain DNA sequences linked to mammalian promoters and transferred into a vector of the pSymvc20 type (FIG. 4D) for antibody expression generating a collection of clones of the pSymvc21 type (FIG. 4E). The CHO-Flp-In cells are either transfected in bulk with a mixture of the pSymvc21 clones or the cells are transfected individually with one pSymvc21 antibody expressing plasmid followed by mixing of the transfected cells expressing the other ovalbumin binding antibodies. The procedure of creating an anti-ovalbumin polyclonal antibody producing cell line can be monitored by DNA sequencing, TaqMan PCR and RFLP analysis of individual antibody expressing cells, as well as ELISA, 2-dimensional (2D) liquid chromatography (LC) and mass spectrometry (MS) of the produced antibody mixture.

Cultivation of Cells and Production of a Recombinant Polyclonal Antibody

The polyclonal cell line produced as described above is grown in suitable media under suitable conditions for expressing the polyclonal protein of interest encoded by the variant nucleic acid sequences inserted into the genome of the cells. The cell cultivation may be performed in several steps. A first step is where the polyclonal cell line is selected for site-specific integrants. When using mammalian cells, the selected cells are then preferably adapted to growth in suspension as well as serum free conditions. This can be performed in one or two steps and with or without selection pressure. When the polyclonal cell line is adapted to the appropriate conditions scaling up can be initiated. At this point a working cell stock can be frozen down. Preferably bioreactors of between 30 and 100 liters are used, but smaller or larger bioreactors may be employed. The suitable production time and choice of bioreactor size are dependent on the desired yield of protein from the batch and expression levels from the cell line. Times might vary from a couple of days up to three month The expressed recombinant polyclonal protein is isolated from the cells or the supernatant. The recombinant protein is purified and characterized according to procedures known by a person skilled in the art. Examples of purification and characterization procedures are listed below.

Purification of a Recombinant Polyclonal Protein from Culture Supernatant

Isolation of specific proteins from culture supernatants is possible using various chromatographic techniques that utilize differences in the physico-chemical properties of proteins, e.g. differences in molecular weight, net charge, hydrophobicity, or affinity towards a specific ligand or protein. Proteins may thus be separated according to molecular weight using gel filtration chromatography or according to net charge using ion-exchange (cation/anion) chromatography or alternatively using chromatofocusing. Similarly, proteins may be separated after hydrophobicity using hydrophobic interaction chromatography or affinity chromatography utilizing differences in affinity towards a specific immobilized ligand or protein. Separation of complex mixtures of proteins may thus be achieved by sequential combination of various chromatographic principles. A mixture of proteins may thus initially be separated according to e.g. net charge using ion-exchange chromatography and proteins of similar net charge may subsequently be separated according to molecular weight using gelfiltration chromatography or after hydrophobicity using hydrophobic interactions chromatography in the presence of a high concentration of a selected salt.

Affinity chromatography combined with subsequent purification steps such as ion-exchange chromatography, hydrophobic interactions and gel filtration has frequently been used for the purification of IgG (polyclonal as well as monoclonal) and TcR from different sources e.g., ascites fluid, cell culture supernatants and serum. Affinity purification, where the separation is based on a reversible interaction between the protein(s) and a specific ligand coupled to a chromatographic matrix, is an easy and rapid method, which offers high selectivity, usually high capacity and concentration into a smaller volume. Protein A and protein G, two bacterial cell surface proteins, have high affinity for the $F_c$ region, and have, in an immobilized form, been used for many routine applications, including purification of polyclonal IgG and its sub-classes from various species and absorption and purification of immune complexes.

Following affinity chromatography, downstream chromatography steps, e.g. ion-exchange and/or hydrophobic interaction chromatography, can be performed to remove host cell proteins, leaked Protein A, and DNA.

Gel filtration, as a final purification step, can be used to remove contaminant molecules such as dimers and other aggregates, and transfer the sample into storage buffer. Depending on the source and expression conditions it may be necessary to include an additional purification step to achieve the required level of antibody purity. Hydrophobic interaction chromatography or ion-exchange chromatography are thus frequently used, in combination with Protein A and gelfiltration chromatography, to purify antibodies for therapeutic use.

In order to purify other classes of antibodies, alternative affinity chromatography media have to be used since proteins A and G do not bind IgA and IgM. An immunoaffinity purification can be used (anti-IgA or anti-IgM monoclonal antibodies coupled to solid phase) or, alternatively, multistep purification strategies including ion-exchange and hydrophobic interaction can be employed.

Structural Characterization

Structural characterization of polyclonal proteins such as antibodies and TcRs requires high resolution due to the complexity of the mixture (clonal diversity and glycosylation). Traditional approaches such as gel filtration, ion-exchange chromatography or electrophoresis may not have sufficient resolution to differentiate among the individual antibodies. Two-dimensional polyacrylamide gel electrophoresis (2D-PAGE) has been used for profiling of complex protein mixtures followed by mass spectrometry (MS) or liquid chromatography (LC)-MS (e.g., proteomics). 2D-PAGE, which combines separation on the basis of a protein's charge and mass, has proven useful for differentiating among polyclonal, oligoclonal and monoclonal immunoglobulin in serum samples. However, this method has some limitations. Chromatographic techniques, in particular capillary and LC coupled to electrospray ionization MS are increasingly being applied for the analysis of complex peptide mixtures. LC-MS has been used for the characterization of monoclonal antibodies and recently also for profiling of polyclonal antibody light chains. The analysis of very complex samples requires more resolving power of the chromatographic system, which can be obtained by separation in two dimensions (or more). Such an approach could be based on ion-exchange in the first dimension and reversed-phase chromatography (or hydrophobic interaction) in the second dimension optionally coupled to MS.

Functional Characterization

A polyclonal protein can for example be characterized functionally through comparability studies with polyclonal proteins with specificity towards the same target or a similar activity. Such studies can be performed in vitro as well as in vivo.

An in vitro functional characterization of a polyclonal antibody could for example be immunoprecipitation which is a highly specific technique for the analytical separation of target antigens from crude cell lysates. By combining immunoprecipitation with other techniques, such as SDS-PAGE followed by protein staining (Coomassie Blue, silver staining or biotin labeling) and/or immunoblotting, it is possible to detect and quantify antigens e.g., and thus evaluate some of the functional properties of the antibodies. Although this method does not give an estimate of the number of antibody molecules nor their binding affinities, it provides a visualization of the target proteins and thus the specificity. This method can likewise be used to monitor potential differences of the antibodies toward antigens (the integrity of the clonal diversity) during the expression process.

An in vivo functional characterization of a polyclonal antibody could for example be infection studies. An experimental animal such as a mouse can for example be infected with a specific virus, towards which a polyclonal antibody has been developed. The degree to which the infection can be inhibited will indicate functionality of the polyclonal antibody.

Therapeutic Compositions

In an embodiment of the invention, a pharmaceutical composition comprising a recombinant polyclonal protein selected from the immunoglobulin super family as it active ingredient is intended for the treatment or prevention of a disease in a mammal such as a disease selected from cancer, infections, inflammatory diseases, allergy, asthma and other respiratory diseases, autoimmune diseases, immunological malfunctions, cardiovascular diseases, diseases in the central nervous system, metabolic and endocrine diseases, transplantation rejections and undesired pregnancy. The mammal is preferably a human, a domestic animal or a pet.

In a preferred embodiment of the present invention, the pharmaceutical composition comprises a recombinant polyclonal antibody or antibody fragment as the active ingredient and a pharmaceutically acceptable excipient.

In another preferred embodiment of the present invention, the pharmaceutical composition comprises a recombinant polyclonal T cell receptor or T cell receptor fragment as the active ingredient and a pharmaceutically acceptable excipient.

For the treatment or prevention of infections, the pharmaceutical composition according to the invention comprises a recombinant polyclonal protein of interest capable of reacting with or binding to an infectious microorganism such as a microorganism selected from bacteria, mycobacteria, virus, mycoplasma, rickettsia, spirochetes, protozoa, fungi, helminthes and ectoparasites.

Recombinant human polyclonal proteins may be administered within a pharmaceutically-acceptable diluent, carrier, or excipient, in unit dosage form. Conventional pharmaceutical practice may be employed to provide suitable formulations or compositions to administer the compounds to patients suffering from a disease, for example, caused by excessive cell proliferation. Administration may begin before the patient is symptomatic. Any appropriate route of administration may be employed, for example, administration may be parenteral, intravenous, Intra-arterial, subcutaneous, intramuscular, intracranial, intraorbital, ophthalmic, intraventricular, intracapsular, intraspinal, intracisternal, intraperitoneal, intranasal, aerosol, suppository, or oral administration. For example, therapeutic formulations may be in the form of, liquid solutions or suspensions; for oral administration, formulations may be in the form of tablets or capsules chewing gum, pasta, compositions suitable for the application onto the skin may be in the form of creams, ointments, lotions, gels, pads or other, compositions suitable for application onto the vaginal or urogenital mucosa may be in the form of vagitories, gels or other and for intranasal formulations, in the form of powders, nasal drops, or aerosols.

The pharmaceutical compositions of the present invention are prepared in a manner known per se, for example, by means of conventional dissolving, lyophilising, mixing, granulating or confectioning processes. The pharmaceutical compositions may be formulated according to conventional pharmaceutical practice (see for example, in Remington: The Science and Practice of Pharmacy (20th ed.), ed. A. R. Gennaro, 2000, Lippincott Williams & Wilkins, Philadelphia, Pa. and Encyclopedia of Pharmaceutical Technology, eds. J. Swarbrick and J. C. Boylan, 1988-1999, Marcel Dekker, New York, N.Y.).

Solutions of the active ingredient, and also suspensions, and especially isotonic aqueous solutions or suspensions, are preferably used, it being possible, for example in the case of lyophilized compositions that comprise the active ingredient alone or together with a carrier, for example mannitol, for such solutions or suspensions to be produced prior to use. The pharmaceutical compositions may be sterilized and/or may comprise excipients, for example preservatives, stabilisers, wetting and/or emulsifying agents, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, poly vinylpyrrolidone or gelatin.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture. If desired or necessary, after the addition of appropriate excipients, into tablets, drage cores or capsules. It is also possible for them to be incorporated into plastics carriers that allow the active ingredients to diffuse or be released in measured amounts.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, drages, tablets or capsules.

The formulations can be administered to human patients in therapeutically effective amounts (e.g., amounts which prevent, eliminate, or reduce a pathological condition) to provide therapy for a disease or condition. The preferred dosage of therapeutic agent to be administered is likely to depend on such variables as the type and extent of the disorder, the overall health status of the particular patient, the formulation of the compound excipients, and its route of administration.

If desired, treatment with recombinant human polyclonal antibodies may be combined with more traditional therapies. For example in the treatment of cancer such combinatorial therapies could take the form of surgery or administration of chemotherapeutics or other anti-cancer agents.

In another embodiment of the invention, the pharmaceutical composition according to the invention comprises a recombinant polyclonal protein of interest capable of reacting with or binding to an infectious microorganism such as a microorganism selected from bacteria, mycobacteria, virus, mycoplasma, *rickettsia*, spirochetes, protozoa, fungi, helminthes and ectoparasites.

Therapeutic Uses of the Compositions According to the Invention

The pharmaceutical compositions according to the present invention may be used for the treatment, amelioration or prevention of a disease in a mammal. Diseases that can be treated with the present pharmaceutical compositions include cancer, infectious diseases, inflammatory diseases, allergy, asthma and other respiratory diseases, autoimmune diseases, cardiovascular diseases, diseases in the central nervous system, metabolic and endocrine diseases, transplantation rejections and undesired pregnancy.

One aspect of the present invention is a method for disease treatment, amelioration or prophylaxis in an animal, wherein an effective amount of the recombinant polyclonal antibody or antibody fragment is administered. In further aspect an effective amount of the recombinant polyclonal T cell receptor or T cell receptor fragment is administered.

An additional aspect of the present invention is the use of a recombinant polyclonal antibody or recombinant polyclonal T cell receptor or fragments of antibodies or T cell receptors for the preparation of a composition for the treatment of diseases selected from a group consisting of a cancer, an infection, an inflammatory disease, an allergy, asthma or other respiratory disease, immunological malfunctions, an autoimmune disease, a cardiovascular disease, a disease in the central nervous system, a metabolic disease, an endocrine diseases, transplant rejection, and undesired pregnancy.

Diagnostic Use and Environmental Detection Use

Another embodiment of the invention is directed to diagnostic kits and kits for environmental detection use as well as methods for using these kits. Kits according to the present invention comprise a recombinant polyclonal protein prepared according to the invention which protein may be labeled with a detectable label or non-labeled for non-label detection. If labeled, the present recombinant polyclonal protein may be added to a sample suspected of containing the target molecule and the presence or absence of the label indicate the presence or absence of the target molecule. The sample to be tested may be a sample of bodily fluid such as blood, serum, plasma, spinal fluid, lymph or urine or a non-mammalian sample such as a sample from an environmental source suspected of harboring a contaminant. Non-mammalian samples may be water, air or contaminated earth. Non-label detection encompasses the measurement of refractive change in BIAcore upon binding, wherein the recombinant polyclonal protein is used to capture the target molecule.

EXAMPLES

The following examples describe how recombinant polyclonal antibodies are expressed and produced in a high-producer cell line, where gene(s)/vector(s) of interest have been inserted by site-specific integration into a pre-characterized chromosomal "hot spot" site.

In the examples, CHO cells were utilized as host cell. The advantages thereof include the availability of suitable growth medium, their ability to grow efficiently to a high density in culture, and their ability to express mammalian proteins such as antibodies in a biologically active form.

In general, transformation of *E. coli* and transfection of mammalian cells according to the subject invention will be performed according to conventional methods. To improve the understanding of the invention, construction of exemplary vectors and their usage in producing a recombinant polyclonal manufacturing cell line for recombinant polyclonal protein expression are described in the examples below.

The following examples illustrate the invention, but should not be viewed as limiting the scope of the invention.

Example 1

Site-Specific Integration Versus Random Integration

For the following transfection experiment, the CHO Flp-In cells (Invitrogen, Carlsbad, Calif.) were used. The efficiency of the system was tested using human secreted alkaline phosphatase (SEAP) as a reporter gene. Two plasmid constructs were prepared:

1. SEAP inserted into pcDNA3.1 hygro+ (Invitrogen, Carlsbad, Calif.) (for random integration)
2. SEAP inserted into pcDNA5/FRT (Invitrogen, Carlsbad, Calif.) (for site-specific integration)

The two plasmid constructs were very similar with respect to regulatory elements, i.e. promoter, polyadenylation etc. which made it possible to, use the plasmids for comparing random integration with site-specific integration.

CHO Flp-In cells were transfected with plasmid construct 1 alone or plasmid construct 2 together with the recombinase-encoding plasmid pOG44 according to the procedure described by Invitrogen. Transfectants were selected using hygromycin and the production of SEAP from pools of transfectants was measured.

Cells transfected by site-specific integration produced approximately 6 times more SEAP than cells transfected by random integration proving the efficiency of the system and the cell line.

Example 2

Design and Preparation of an Expression Vector for Site-Specific Integration in a Host Cell An expression vector suitable for site-specific integration into a hot spot chromosomal region of a host cell may be assembled comprising the following DNA elements:
a) an FRT recombination site linked to the hygromycin resistance gene,
b) a pUC origin of replication,
c) an ampicillin resistance gene (bla),
d) a bla-promoter allowing expression of the ampicillin (bla) resistance gene,
e) gene(s), encoding a protein of Interest (GOIs),
f) promoter(s) allowing expression of the GOI, and
g) optionally, additional transcriptional or translational regulatory elements, such as enhancers or UCOE's, for increased expression at the site of integration or an IRES.

To provide a better understanding of the construction of the expression vector, each of the elements are described in more details:
a) An FRT recombination site linked to the hygromycin resistance gene for Flp recombinase-mediated integration and selection of a cell line with a majority of single integrants was used. The hygromycin gene was neither preceded by a promoter nor equipped with a transcription initiating codon, but a polyadenylation signal was added 3' of the gene. The FRT site used was 5'-gaagttcctattccgaagttcctat-tctctagaaagtataggaacttc-3' (SEQ ID NO 1).
b) A pUC origin of replication was included to permit high copy number replication in an *E. coli* host cell.
c) An Ampicillin (bla) resistance gene (β-lactamase) allowing selection of *E. coli* transformants was included.

d) A bla-promoter allowed expression of the ampicillin (bla) resistance gene in *E. coli*.
e) GOI encoding a protein of interest, e.g., a recombinant polyclonal protein, antibody, the heavy and light chains of an antibody, as well as nucleotide sequences that encode all or a portion of either the constant region or variable region of an antibody molecule, and optionally all or a portion of a regulatory nucleotide sequence that controls expression of an antibody molecule were included.

Immunoglobulin loci for heavy chains may include but is not limited to all or a portion of the V, D, J and switch region (including intervening sequences, also known as introns) and flanking sequences associated with or adjacent to the particular heavy chain constant region gene and it may include regions located within or downstream of the constant region (including introns).

Immunoglobulin loci for the light chains may include but are not limited to the V and J regions, their upstream flanking sequences, and intervening sequences (introns) associated with or adjacent to the light chain constant region gene, and it may include regions located within or downstream of the constant region (including introns).

For the modification of all or a portion of a constant region of an antibody, modifying sequences of the invention may include, but are not limited to an antibody constant region having a particular effector function, class and/or origin (e.g., IgG, IgA, IgM, IgD, or IgE constant regions of a human immunoglobulins or any other species) or a portion of a constant region which modifies the activity or properties of the constant region of the antibody; as well as genes which encode other molecules that confer some new function to a modified antibody molecule, e.g., an enzyme, toxin and the like.

The gene(s) encoding a protein of interest may be operatively linked to nucleotide sequences encoding functional leader sequences directing the gene product to the secretory pathway.

Further, 3' to the GOI encoding the protein of interest, e.g., such as a polygonal antibody comprising heavy and light chains, there may be strong polyadenylation signals. The use of the mouse isotype IgG1 in the following examples is for illustrative purposes and is not intended to limit the scope of the invention.

f) Promoters allowing expression of the GOI are provided. Therefore, a cassette comprising promoter and enhancer elements for expression is described. In the expression vector, each of the antibody genes may be preceded by their own mammalian promoter elements directing high level expression of each of the two chains, whether uni-directionally, bi-directionally or a tail-to-tall orientation of transcription cassettes is used.

In a bi-directional orientation of expression, a head-to-head promoter configuration can be used (construction of such a system is described in details in U.S. Pat. No. 5,789, 208, which is incorporated by reference in its entirety). In a unidirectional expression system, two promoters or one promoter combined with e.g., an IRES sequence can also be used for expression.

For construction of head-to-head promoters, a Pfu PCR amplification of the promoters is performed individually. The 5'-primer will initiate on the 5'-most base of the promoter, the 3'-end primer will include a unique restriction site, such as, a XbaI site. Following PCR amplification, the fragments may be separated on an agarose get, and isolated from the gel using QiaQuick columns (Qiagen). This is followed by an XbaI restriction digestion, heat inactivation at 65° C. for 20 minutes, and column purification of the fragments using QiaQuick. The fragments are then mixed and ligated together using *E. coli* ligase (New England Biolabs (NEB)), an enzyme that preferentially ligates sticky ends. The ligation mix is PCR amplified with the 5'-primers of each promoter to yield the complete head-to-head promoter (promoter A/promoter B) fragment. This fragment is kinased with T4 polynucleotide kinase (PNK) (NEB), the enzyme is heat inactivated at 65° C. for 20 minutes, and the fragment is ligated (blunt end) into the vector of interest (PCR amplified pSymvc10 (see FIG. 4) fragment, where the primers used for amplification anneal on each side of the promoter region amplifying everything except the promoter) using T4 ligase (NEB).

Figure 1:
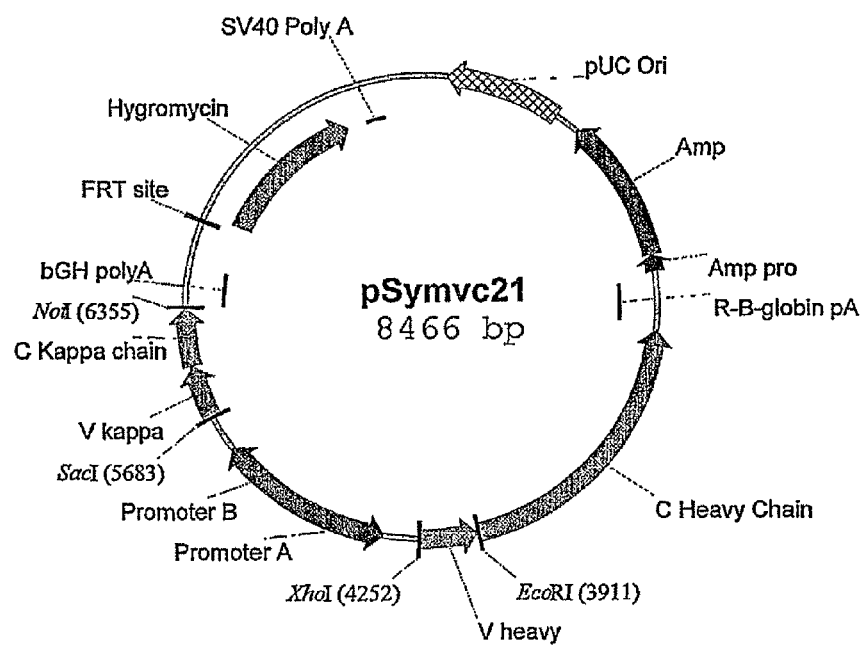
FIG. 1: Schematic representation of a "head-to-head promoter" expression vector comprising the following elements: Amp pro=A promoter allowing expression of the ampicillin resistance gene. Amp=An ampicillin resistance gene. pUC origin=A pUC origin of replication, Restriction enzyme sites: NotI and EcoRI. Promoter A/Promoter B=head-to-head promoter cassette including leader sequences (e.g., CMV/ MPSV). V Heavy=Sequence coding for the variable heavy chain of a GOI. C Heavy Chain=Sequences coding for the constant heavy chain (e.g., the sequences for mouse IgG1 or IgG2B constant heavy chain). R-B-globin pA=Rabbit β-globin poly A sequence. bGH polyA=Bovine Growth Hormone poly A sequence. V Kappa=Sequence coding for the variable kappa of a GOI. C Kappa chain=Sequence coding for the constant kappa chain. FRT site=A FRT recombination site. Hygromycin=gene for hygromycin resistance. SV40 poly A=poly A signal sequence.
Figure 2:
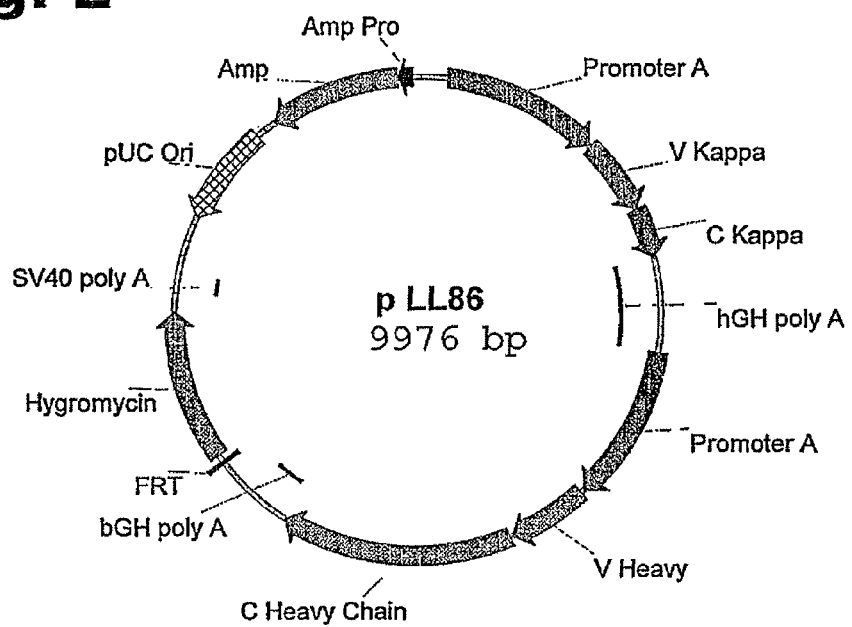
FIG. 2: Schematic representation of an expression vector for uni-directional expression comprising the following elements: Amp pro=A promoter allowing expression of the ampicilin resistance gene. Amp=An ampicillin resistance gene. pUC ori=A pUC origin of replication. Promoter A=mammalian promoter including leader sequences (e.g., AdMLP). V Heavy=Sequence coding for the variable heavy chain of a GOI. C Heavy chain=Sequences coding for the constant heavy chain (e.g., the sequences for mouse IgG1 constant heavy chain). hGH poly A=Human growth hormone poly A sequence. bGH polyA=Bovine Growth Hormone poly A sequence. V Kappa=Sequence coding for the variable kappa light chain of a GOI. C Kappa=Sequence coding for the constant kappa chain. FRT=A FRT recombination site. Hygromycin=gene for hygromycin resistance. SV40 poly A=poly A signal sequence. The sequences of hGH poly A and promoter A could be replaced by an IRES structure.

FIGS. 1 and 2 show expression vectors comprising promoters for bi-directional and uni-directional, respectively. These promoters intend to illustrate, but not limit, the promoter choice in the invention.

g) The expression vector can carry additional transcriptional and/or translational regulatory elements, such as enhancers and/or UCOE's, for increased expression at the site of integration and/or IRES.

Example 3

Evaluation of Polyclonality Preservation in the Manufacturing System Developed

In order to be able to evaluate the stability and reproducibility of the manufacturing system, a cell line expressing a polyclonal composition of distinct antibodies in known combination was prepared. The polyclonal antibody composition was termed the mini six composition. The library of nucleic acid sequences encoding the mini six composition was termed the mini six library.

(a) Clone Origin

The following sequences encoding Fab fragments (the genes of interest) with reactivity against antigens 1-6 were used in this example:

1. Ovalbumin (OVA). The Fab encoding fragments were selected from a murine anti-OVA phage display library.
2. Alkaline phosphatase (AP). The Fab encoding fragments were selected from a murine anti-AP phage display library.
3. $\beta_2$-microglobulin ($\beta_2$m). The Fab encoding fragments were cloned from the hybridoma BBM.1 (a gift from Dr. L. ø. Pedersen, Denmark), which was generated against $\beta_2$m.
4. Human haptoglobin (HAP). The Fab encoding fragments were selected from a murine anti-human haptoglobin phage display library.
5. Factor VIII (FVIII). The parental monoclonal antibody of this Fab fragment was a FVIII F25 monoclonal antibody (gift from Novo Nordisk, Denmark). The DNA encoding the $V_H$ and complete Kappa chains of this Fab fragment was sub-cloned into a phagemid, followed by insertion of the prokaryotic promoter cassette into the construct.
6. Hen egg lysozyme (LYS). This construct was generated from the D1.3 scFv clone (Boulot, G. et al., *J. Mol. Biol.*, 213(4) (1990) 617-619), by PCR amplification of $V_H$ and $V_K$ fragments and cloning into a phagemid.

The phagemid clones exist either in transformed *Escherichia coli* strain TG1 glycerol stocks (kept at −80° C.) or as phagemid DNA preparations.

(b) Rflp Analysis and DNA Sequencing of the Mini Six Library.

The nucleotide sequences encoding the heavy chains of the Fab fragments were analyzed by RFLP as follows: The band patterns obtained after digest of the PCR generated fragments with the NlaIII and Hinf I enzyme were examined. The different Fab fragment encoding sequences exhibited very different and easily distinguishable patterns. The nucleotide sequences encoding the $V_H$ and $V_L$ fragments were sequenced and sequences corresponding to the RFLP pattern were found. Furthermore, the nucleotide sequences encoded open reading frames and translated into well-defined polypeptides.

(c) Elisa Analysis of the Mini Six Composition

The Fab fragments expressed from the clones were analyzed using ELISA, in which all Fab fragments were analyzed for reactivity with all antigens. Fab expression was monitored using an anti-kappa ELISA. All Fab fragments were tested in duplicate in ELISA. All clones expressed Fab fragments, and the Fab fragments reacted specifically with their relevant antigen. No background problems were found in the ELSA analyses.

The six phagemid clones exist in individually transformed *Escherichia coli* strain TG1 glycerol stocks, which were used in the model system for inoculation as described below.

(d) Design of a Polyclonal Model System with Six Distinct Antibodies in Known Combination.

The six selected Fab-expressing clones (clones expressing Fab fragments of anti-OVA, anti-AP, anti-$\beta_2$m, anti-HAP, anti-FVIII, and anti-LYS) were characterized by testing the reactivity of the expressed Fab fragments against the relevant antigens. These clones formed part of a polyclonal model system for testing the expression and production of six distinct antibodies in a known combination (the mini six composition). All Fab fragments encoding nucleotide sequences (the mini six library) were transferred into a phagemid vector (illustrated by pSymvc10, FIG. 4A).

(d.1) Individual Transfer of the GOI's from the Phagemid Vector into a Vector for Mammalian Expression The transfer of the genes of interest (the mini six library) from a phagemid vector to a vector for mammalian expression was, in this example, performed by a two-step procedure. The first step was to replace the prokaryotic promoters with a mammalian promoter cassette in a head-to-head orientation. This step was followed by transferring the variable region of the GOI's, the promoter cassette and the constant kappa to the expression vector as described in detail below, and illustrated in FIG. 4.

The head-to-head promoter cassette (promoter A/promoter B) was inserted into the phagemid vector for each clone by using a SacI/XhoI digestion followed by a ligation resulting in exchange of promoters from bacterial to mammalian. An EcoRI and NotI digest was then used to move the variable heavy chain, the head-to-head promoter cassette (promoter A/promoter B) and the complete kappa chain (EcoRI/Not I fragment) from the phagemid vector into the expression vector.

An example of the individual transfer of each clone is given with the flow chart in FIG. 4. This figure shows plasmid pSymvc10 where the heavy and kappa coding sequences of interest (e.g., gc032 OVA) are present in the phagemid vector into which the head-to-head mammalian promoter cassette construct was ligated to replace the bacterial promoters using a SacI/XhoI fragment transfer generating pSymvc12.

From this construct, the variable heavy chain-coding sequence including the promoter cassette and the whole of the kappa chain coding sequence was transferred into the mammalian isotype-encoding vector (pSymvc20) by a NotI/EcoRI transfer. The resulting vector (pSymvc21) expressed the mouse antibody of interest (e.g., anti-OVA IgG1 antibody).

The variable heavy chain coding sequence, the mammalian promoter cassette and the entire kappa chain coding sequence from each of the six clones were transferred individually by a NotI/EcoRI transfer resulting in the mammalian expression vector pSymvc21, which expresses each of the GOI encoded antibody sequences as mouse IgG1 antibodies.

The six individual pSymvc21 clones containing the six GOIs were kept as TG1 glycerol stocks.

For transfection into CHO Flp-In cells, the TG1 stocks were propagated individually, and after $OD_{600}$ normalization for the number of *E coli* cells, the six cultures were mixed and used for plasmid preparation. This plasmid preparation comprising the six GOIs (the mini six library) was used for bulk transfection of mammalian cells for recombinant polyclonal protein expression.

(d.2) Mass Transfer of the GOI's from Phagemid Vectors into Vectors for Mammalian Expression The GOIs (the mini six library) (here the EcoRI/NotI fragments), which were located in phagemid vectors and coding for six distinct Fab fragments (anti-OVA, anti-AP, anti-$\beta_2$m, anti-HAP, anti-FVIII, and anti-LYS), were transferred in-mass as a mixture of the six vector constructs into vectors for mammalian expression resulting in a mixture of six distinct expression vectors.

The experimental procedure concerning the mass transfer follows the procedure described in (d.1) with the exception that it was performed in-mass, i.e. all six GOIs (encoding the varable heavy chains, including the head-to-head promoter cassette and complete kappa chains) were transferred simultaneously as a mixture of the six phagemid vectors.

Plasmid Preparations of the Mini Six Library

Plasmid Preparation 1 refers to a plasmid preparation of a mix of the six phagemid vectors (with the antibody coding sequences contained in the vector pSymvc10).

Plasmid Preparation 2 refers to a plasmid preparation of six phagemid vectors with the coding sequences contained in the vector pSymvc12 after mass transfer step 1 (see FIG. 4C), which results in the exchange of the prokaryotic promoters with the mammalian promoter cassette constructs.

Plasmid Preparation 3 refers to a plasmid preparation after mass transfer step 2 (see FIG. 4D), which affords exchange of the variable heavy chain, the head-to-head promoter cassette, and the complete kappa chain from the pSymvc12 to the mammalian expression vector (pSymvc21), thus allowing expression of the six selected antibodies as full length mouse IgG1 antibodies.

Genotyping of TG1 Cells Transformed with Plasmid Preparations Used in Mass Transfer TG1 cells were transformed with the mini six library in bulk by electroporation and after an overnight incubation on 2xYT (Sigma Y 2627) plates, individual colonies were picked. In each experiment 180 colonies were picked and incubated in 96 well formats in 2xYT liquid medium for 4 hours. Aliquots of the cultures were diluted with water, denatured and used as template in PCR. In all experiments, the variable heavy chain was amplified. Primer sequences for the phagemid vectors (pSymvc10-type) were:

```
5'-GCATTGACAGGAGGTTGAGGC-3'    (SEQ ID NO 2)
and

5'-GCTGCCGACCGCTGCTGCTGGTC-3'  (SEQ ID NO 3)
```

Primers for vectors with mammalian promoter cassette were (pSymvc12-type):

```
5'-GCATTGACAGGAGGTTGAGGC-3'    (SEQ ID NO 4)
and

5'-GTGCCACTCTGAGGTTCAG-3'      (SEQ ID NO 5)
```

Primers for pSymvc21 constructs were:

```
5'-CAAATAGCCCTTGACCAGGC-3'        (SEQ ID NO 6)
and

5'-GTGTCCACTCTGAGGTTCAG-3'        (SEQ ID NO 7)
```

All PCR products were digested with both NlaIII and HinfI to ensure unambiguous genotyping. The digestion fragments were analyzed by agarose gel electrophoresis and bands were visualized by EtBr staining. The number of individual genotypes resembled by the fragment pattern determined by RFLP corresponds to the number of individual colonies representing each of the six antibodies among the total number of picked colonies.

(d.2a) Mass Transfer from the Phagemid Vector to a Mammalian Vector after DNA Amplification in E. Coli Cells (Two-Step Amplification Method)

The Plasmid Preparation 1 was prepared from each of the six E. coli TG1 glycerol stocks, containing one of the six phagemid vectors constituting the mini six library. The stocks were propagated individually, and after $OD_{600}$ normalization for the number of E. coli, the six cultures were mixed in equal amounts and used for plasmid preparation resulting in Plasmid Preparation 1. The genotype distribution of the six phagemid vectors in Plasmid Preparation 1 was tested by transformation into electrocompetent TG1 cells and subsequent RFLP analysis. The distribution of the different genotypes in TG1 cells is shown in FIG. 5.

The Plasmid Preparation 1 comprising the polyclonal phagemid vector expressing an equal mixture of the six selected Fab fragment genotypes was digested with SacI/XhoI. Then the head-to-head promoter cassette (CMV promoter/MPSV promoter) was inserted by ligation. The genotype distribution of the vectors after the promoter exchange in the vector was tested in TG1 cells after transformation with DNA from the ligation step (FIG. 6).

The cells were plated and grown on large (245 mm×245 mm) 2×YT agar plates and the Plasmid Preparation 2 was prepared to generate the phagemid vector now containing the head-to-head promoter cassette (pSymvc12).

From the Plasmid Preparation 2, the variable heavy chain coding sequence, including the promoter cassette and the complete kappa chain sequence was cut out from the phagemid vector by a NotI/EcoRI digest and transferred into a vector (pSymvc20) already containing the constant region domains of mouse IgG1. This resulted in a collection of psymvc21 vectors, which expresses the variable region of the six selected antibody clones as full-length mouse IgG1 antibodies.

The promoter transfer can alternatively be performed in the mammalian vector encoding an isotype, reversing the order of restriction digest starting with NotI/EcoRI for transfer of the DNA of interest to the mammalian vector and then SacI/XhoI restriction digest fragment for insertion of the promoter region.

The distribution of genotypes after transferring the variable heavy chain coding sequence, the promoter cassette and the whole kappa chain encoding sequence into the expression vector was tested by transforming TG1 cells with DNA from the second ligation step (FIG. 7). Cells were plated on large (245 mm×245 mm) 2×YT agar plates and Plasmid Preparation 3 was prepared (pSymvc21), in which the variable region of the six clones are expressed in the context of a mouse IgG1 antibody framework.

The Plasmid Preparation 3 can be used for the bulk transfection of mammalian cells to generate a recombinant polyclonal manufacturing cell line for recombinant polyclonal antibody expression.

The results of the mass transfer from the phagemid vector to an isotype-encoding mammalian vector after DNA amplification in E. coli cells showed that it was possible to obtain a balanced distribution of the six vector constructs after they had been propagated individually and mixed (Plasmid Preparation 1, FIG. 5). The six constructs, after exchange of promoter cassette (Plasmid Preparation 2, FIG. 6) as well as after insertion into a mouse IgG1 isotype-encoding vector (Plasmid Preparation 3, FIG. 7), were all detectable at comparable levels.

(d.2b) Mass Transfer from a Phagemid Vector to a Vector for Mammalian Expression without DNA Amplification in E. Coli after the Plasmid Preparation 1 Step (One-Step Amplification Method)

DNA from the Plasmid Preparation 1 (here was used 25 µg) comprising the polygonal phagemid vector (pSymvc10) expressing an equal mixture of the six selected Fab fragment genotypes was digested with SacI/XhoI for exchange of promoters. The SacI/XhoI vector fragment was purified and ligated with the head-to-head promoter cassette (CMV promoter/MPSV promoter). After the exchange of promoters without performing any amplification, the vector with CMV/MPSV promoter cassette was digested with NotI/EcoRI for cutting out the whole region with the variable heavy chain encoding sequence. Including the promoter cassette and the entire kappa chain encoding sequence from the phagemid vector for mass transfer into a vector for mammalian expression. After ligating the NotI/EcoRI fragment encoding the variable heavy chain, the promoter cassette and the kappa chain into a mouse IgG1-encoding vector (pSymvc20), an expression vector, which expresses the variable region of the six selected clones in the context of mouse IgG1 full length antibodies was obtained. The composition of this expression vector is illustrated in FIG. 1.

After the mass transfer resulting in the promoter exchange in the vector and transfer of the nucleotide sequences encoding the variable heavy chain, the promoter cassette and the complete kappa chain into a vector for mammalian expression, the distribution of genotypes was tested by transformation of TG1 cells with plasmid from the second ligation step. Cells were plated on large (245 mm×245 mm) 2×YT agar plates and a plasmid preparation of this double digestion/ligation Plasmid Preparation was prepared (vector pSymvc21, in which the variable region of the six clones are expressed in the context of mouse IgG1 antibodies, corresponding to Plasmid Preparation 3 from d.2a). The genotype distribution in TG1 cells after transformation with the plasmid preparation from the one-step amplification method is shown in FIG. 8.

The one-step amplification method might introduce some scrambling among the heavy and light chains from the six Fab encoding sequences resulting from the generation of undesired ligation products, which are normally omitted during amplification in E. coli. However, if such scrambling occurs, a screening step can be introduced to ensure that sufficient clonal diversity is maintained.

(d.2c) Direct Transfection of Mammalian Cells Following Promoter Exchange

The product from the plasmid preparations of the mini six library from either the two-step amplification method or one-step amplification method can be used directly to transfect mammalian cells in bulk for recombinant polyclonal antibody expression.

(d.3) Testing of the Transfected Mammalian Cells

The known antibody combination of the mini six polyclonal model system can be used to test and ensure that the mass transfer and transfection into mammalian cells occur in a way that maintains the clonal diversity and without introducing bias in the composition of the antibody variable sequence genotypes during transfection and subsequent culturing. The methods by which the genotypic composition will be monitored throughout the process of mass transfer, bulk transfection and mammalian expression, can comprise the following:

DNA sequencing of isolated clones
RFLP analysis of individual clones
ELISA of the produced antibody mixture
Mass spectrometry of the produced antibody mixture
Taqman PCR of the relative composition of the genomic sequences and mRNA expressing the different heavy and light chains Deviations in the genotypic composition introduced during the transfection process, should they occur, could be caused by random integration or multiple integrants. As described in the detailed description it is not likely to cause problems when using a host cell line pre-designed for site-specific integration. However, it can be controlled in a variety of ways. Selection against integration in a random genomic location (a location other than the site-specific location) may be done using very low quantities of DNA, e.g., 1 µg/$10^7$ cells when performing transfection with Lipofectamine or 0.2 µg/$10^7$ cells when performing transfection by electroporation. Also, the DNA to be integrated may be supplied in supercoiled form; a form known to be unfavorable for random integration.

Single or multiple integrations outside of the pre-designed target site will be eliminated by negative selection, because the selectable marker will be present in the genome without a promoter or a start codon. Thus, recipients of these random integration events do not survive the selection process.

Transformants having multiple integrations where one of the recombination events occurs at the target site will survive the selection process; however, the probability of this type of multiple integrations is extremely low. This event would, therefore, lead to minimal scrambling of the polyclonal protein. Further, because there would be 100 to 1000 other clones encoding the same recombinant polyclonal protein, even if ectopic expression is high, the scrambling effect would be less than about 1% if multiple integrations occurred. As mentioned previously, the probability of ectopic integration can be reduced by reducing the quantity of DNA used in the method.

The least likely event is a multiple tandem integration at the target site. Using the Flp recombinase system described here, this type of event will be rare because the excision activity from the chromosome is significantly higher than the integration activity. However, should tandem integration occur at an unacceptably high frequency, the Flp system can be exchanged for one in which only a single copy insert is possible (see, for example, WO 99/25854; incorporated by reference).

(e) Expression of the Six Distinct Antibodies in Known Combination in Mammalian Cells Generally in order to minimize variable proliferation rates, it is preferable to integrate each specific GOI (in this case each individual member of the mini six library) into at least 100, preferably 1000 and most preferred into 10000 cells. A polyclonal cell line containing a large number of individual cells expressing the same GOI (for all the GOI's) is statistically expected to be less influenced by differences in proliferation rates of individual cells and have reduced possibility of bias in the final polyclonal protein composition.

Further, it might be an advantage to ensure a homogeneous host cell line for the expression. This can be achieved by sub-cloning the host cell line prior to transfection. This process is described in the paragraph regarding clonal diversity.

For polyclonal libraries in which further bias control is desirable, the final composition of the polyclonal protein product can be controlled by introducing an inducible transcriptional control element into the expression vector platform. Suitable inducible control elements include, for example, BD Tet on/off (BD Bioscience, Franklin Lakes, N.J.) and GeneSwitch (Invitrogen, Carlsbad, Calif.). These transcriptional switches can be induced at an appropriate time point (e.g., when the pool of cells is fully expanded) to minimize any proliferation bias due to variation in gene expression or the protein product. The present experiment was not performed with such control elements.

After transferring the six selected GOI from the phagemid vector to the mammalian expression vectors, either individually as described in (d.1) or by mass transfer as described in (d.2), the mammalian expression vectors were used for transfection into a hot spot in a CHO-Flp-In cell line by using site-specific integration for expressing the six distinct antibodies as described below.

For the individually transferred GOI (d.1), plasmid DNA's were propagated individually and used for individual transfection into CHO Flp-In cells or the TG1 stocks were propagated individually, and after $OD_{600}$ normalization for numbers of *E. coli* cells, the six cultures were mixed and used for plasmid preparation. This plasmid preparation containing the six genes of interest was used for bulk transfection of mammalian cells for recombinant polyclonal antibody expression.

For the mass transferred GOI (d.2a or d.2b) plasmid DNA's are either transfected into CHO-Flp-In cells or amplified and purified (Plasmid Preparation 3) according to the procedure described in (d.2a or d2.b) and then used for bulk transfection.

(e.1) Cell Culture

The CHO Flp-In host cell line (Invitrogen, Carlsbad, Calif.) was maintained in Ham's F-12 medium, with the addition of gltamine (2 mM) and FCS (10%) and 100 µg/ml Zeocin (Invitrogen, Carlsbad, Calif.). For sub-culturing, the cells were detached by trypsin and split according to manufacturer's instructions. Cells were grown at 5% $CO_2$, 37° C. Medium and medium additives were from Gibco.

This cell line stably expresses the lacZ-Zeocin fusion gene, rendering the cells resistant to the antibiotic Zeocin, a resistance that upon site-specific integration of a foreign gene will be lost. The cells contain a single copy of the Flp Recombination Target (FRT) site, and are thus ready to be used as host cell line for site-directed integration by use of the Flp-In system (Invitrogen, Carlsbad, Calif.).

(e.2) Transfection of CHO Cells

Tissue culture plates with 6 wells were inoculated with $4.0 \times 10^5$ CHO-Flp-In cells/well, and incubated O/N at 37° C./5% $CO_2$. Transfection of these cells was performed testing different transfection methods using FuGENE™6 (Roche), Lipofectine™, LipofectAmine™, or LipofectAMINE 2000™ (Gibco) according to the manufacturer's instructions. In this example, LipofecAMINE 2000™ was used as transfection reagent. Briefly, on the day before the transfection, exponentially growing CHO-Flp-In cells were seeded as described above and incubated O/N at 37° C./5% $CO_2$. Wells with an 85-95% cell confluence were used for the co-transfection.

Two tubes with the following contents were prepared:

Tube 1: 0.5 µg of an individual expression vector with GOI described in (d.1) (e.g., pSymvc21 with OVA)+4.5 µg mp040 (a maxi preparation of pOG44) (a plasmid expressing recombinase Flp) were added to 250 µl Optimem (1.5 ml Eppendorf tubes).

Tube 2: 7.5 µl LipofectAMINE 2000™ was added to 250 µl Optimem (1.5 ml Eppendorf tubes) and incubated at room temperature (RT) for 5 min.

The content of tube 2 was transferred to tube 1 followed by incubation at RT for 20 min.

The DNA-Lipofectamine complexes were transferred to the wells with cells according to the manufacturer's instructions.

After 24 h, the cells were detached by trypsin, split (1:3) and distributed to a T-25 flask and to 100 mm petri dishes and cultivated in fresh Nutrient Mixture F-12 Ham+10% FCS+2 mM L-Glutamine medium with 900 µg Hygromycin B/ml as selection pressure.

(e.3) Selection of Site-Specific Integrants and Sub-Cultivation of Transfected Cells Cells were cultivated under Hygromycin B selection pressure for two to three weeks, in this period cells were refreshed every 2 to 4 days with new medium containing the same concentration of selecting agent. The surviving pool of cells in the T-25 flask and in Petri dishes were detached by trypsin, spilt (1:6) and distributed to T-flasks for further propagation under the above mentioned selection pressure. Some single clones were picked (using so-called cloning cylinders) from the Petri dishes containing the transfectants generated according to the method described in (d.1), and transferred to new wells for propagation and use in expression level studies.

Each pool of cells or single clones, that was resistant to the threshold Hygromycin B concentration, was subsequently grown to confluence in 6-well plates replated in Petri dishes, T-25, T-80 and T-175 flasks in their respective medium plus Hygromycin B. When exponentially growing cells reached 80% confluence in T80 tissue culture flasks, vials of each cell line were frozen and stored in liquid nitrogen $N_2(L)$-freezer.

For transfection with a mixture of plasmids containing the six genes of interest (the mini six library), the six individual cultures were normalized at $OD_{600}$ for numbers of *E. coli*, mixed and used for a polyclonal plasmid preparation containing the six genes of interest. A transfection procedure using 7.5 times as much of the reagents and cells described above was carried out, producing a recombinant polyclonal cell line expressing a mixture of the six distinct antibodies.

The six cell lines expressing individual members of the selected antibodies and the cell line expressing the mixture of the six distinct antibodies were during cultivation and propagation tested for antibody production by antigen-specific ELISA.

(f) Monitoring the Composition of a Polyclonal Cell Line Expressing Six Distinct Antibodies of Known Combination By generating a mixture of the six selected genes of interest situated in expression vectors followed by bulk transfection and site-specific integration into CHO-Flp-In cells, a polyclonal cell line expressing six distinct antibodies was generated.

The cell line was followed for 34 days in which genotype distribution, antibody expression and proliferation rates were followed. Results are described below.

(f.1) Genotype Distribution of the Six Selected Genes of Interest in Cho-Flp-In Cells Transfected with the Plasmid Preparation from the $OD_{600}$ Normalized Mixture of Cells.

The polyclonal CHO-Flp-In cell line was trypsinized and the cell suspension diluted to 10 cells/ml. Hereafter, 200 µl were transferred to each well of a total of ten 96-well plates. Approximately 10 days later, wells with single colonies were identified by microscopy. Wells with single colonies were washed 1× in PBS and 50 µl water was added. Plates were incubated at 80° C. for 10 min and lysates were transferred to another 96-well plate. Ten µl of the lysates were used in 25 µl OneStep RT-PCR (Qiagen) with the following primers:

```
5'-CAAATAGCCCTTGACCAGGC-3'     (SEQ ID NO 6)
and

5'-GTGTCCACTCTGAGGTTCAG-3'     (SEQ ID NO 7)
```

RFLP was performed using HinfI and NlaIII on 10 µl if of RT-PCR mixtures in 15 µl reactions that were incubated at 37° C. for 2 hours. The digestion fragments were visualized using agarose gel electrophoresis followed by EtBr staining of the gel. The genotype distribution of cells producing anti-OVA, anti-AP, anti-$β_2$m, anti-HAP, anti-FVIII, and anti-LYS was followed over time (days 16 and 34 after transfection), see FIG. 9.

(f.2) Elisa of Samples Derived from CHO-Flp-In Cells Transfected with the Plasmid Preparation from the $OD_{600}$ Normalized Mixture of *E. Coli* (d.1)

The polyclonal CHO-Flp-In cell line (e.3) was trypsinized and 3×10⁶ cells were plated in T-75 flasks in F-12 HAM+10% b FCS+2 mM L-glutamine and 900 µg hygromycin. Medium was changed every day and at day 3 supernatants were selected for ELISA. Antigens, (β2-microglobulin (a gift from University of Copenhagen), alkaline phosphatase (Sigma), ovalbumin (Sigma), factor VIII (a gift from Novo Nordisk, Denmark), hen egg white lysozyme (Sigma), and haptoglobin (Sigma)) were diluted in 50 mM carbonate buffer to 10 µg/ml. ELISA plates were coated with antigen (50 µl to each well) and incubated O/N at 4° C. Wells were washed 4 times with washing buffer (1×PBS/0.05% Tween 20) and blocked for 1 hour with 2% skim milk powder in washing buffer (100 µl to each well). 50 µl samples were added to the wells and plates incubated for 1 hour at RT. Plates were washed 4× and secondary antibodies (Goat anti-mouse IgG/HRP conjugate (Sigma)) were added for 1 hour followed by 4× wash. The ELISA was developed with TMB substrate (50 µl in each well, DAKO S1600) for 5 min and reactions stopped by adding 50 µl 1 M $H_2SO_4$. Plates were read immediately at 450 nm. Data demonstrating expression of all six antibodies of interest in lysates derived on day 34 post-transfection with the mixture of expression vectors encoding the six genes of interest is shown in FIG. 10. It should be noted that since the data presented in FIG. 10 is derived from six different antigen-specific ELISA assays, the OD450 readings are not directly comparable in terms of antibody quantity.

Antibody expression levels were further analyzed by anti-kappa coat ELISA in pools of CHO-Flp-In cells transfected with each individual GOI or the mixture of the six GOI. The result is shown in FIG. 11. This shows that the antibody expression levels are comparable among the individually transfected cell lines (e.g. a cell line transfected with an anti-$β_2$m encoding vector expresses a comparable amount of antibody compared to a cell line transfected with a vector encoding anti-AP antibody). The term pools of CHO-Flp-In cells transfected with individual GOI, is used here because the individual cell lines are not derived from single clones, but pools of clones as described in e.3.

(g) Conclusions from the Experiment

Firstly, these evaluations (tests) of preservation of the polyclonality in the manufacturing system showed that mass transfer of the six selected genes of interest from the mini six library (encoding anti-OVA, anti-AP, anti-β₂m, anti-HAP, anti-FVIII, and anti-LYS) from phagemid vectors into mammalian expression vectors was possible without introduction of selection or proliferation bias (FIG. 7), thereby ending up with comparable frequencies of the six selected genes of interest.

Secondly, bulk transfection of CHO-Flp-In cells with a mixture of the constructs containing the six selected genes of interest also resulted in comparable distribution of the constructs in isolated mammalian cells. The genotype distributions of the six selected genes of interest over time (day 16 and 34 after transfection) were also similar (FIG. 9), indicating that the expression system up to day 34 maintained the original, equal distribution of the six genotypes, without introducing proliferation bias.

Thirdly, the cells transfected in bulk with the mixture of the six genes of interest showed expression of all six antibodies, as examined by antigen-specific ELISA on supernatants from cells 34 days after transfection (FIG. 10). The ELISA results for the different antigens are not directly comparable in terms of antibody amounts, due to different binding affinities.

However, a capture ELISA based on coating with goat anti-mouse kappa chain antibody performed on supernatants from a) the six individually transfected CHO-Flp-In cell lines generated using the vector preparation as described in (d.1) and b) on supernatants of the polyclonal cell line expressing a mixture of the six selected genes of interest showed comparable antibody expression levels from the six genotypes.

In summary, it has been demonstrated that it is feasible to transfer a polyclonal GOI in mass from a phagemid vector to a mammalian expression vector. This has previously been described by Sharon (U.S. Pat. No. 5,789,208). Furthermore, a mixture of mammalian expression constructs could be transfected into mammalian cells in bulk and maintained at a comparable frequency at least up to day 34 post-transfection.

Example 3A

Evaluation of Polyclonality Preservation in Cell Cultures Generated by Bulk Transfection of a Sub-Clone from the CHO-Flp-In Cell Line with the Mini Six Library
(a) Sub-Cloning of "Original" CHO Flp-In Cell Line The original CHO Flp-in cell line (Invitrogen) was cultured as described (Example 3 section e.1). After trypsination cells were counted and plated with 1 cell per well in a 96-well culture plate. Approximately 14 days later 20 wells with single colonies were identified and cells were trypsinated and transferred to 24-well plates. One of the sub-clones, CHO-Flp-In clone 019, was selected for future studies after characterization of growth behavior as well as expression levels.
(b) Bulk Transfection and Selection of Cho-Flp-In Clone 019 Cells Transfection was performed in triplicate, and selection of the CHO-Flp-In clone 019 cells were essential carried out as described (Example 3, section e.2 and e.3), with the exception that a Neomycin selection marker replaced the Hygromycin marker in pSymvc21 (FIG. 4.*e*). Consequently, Geniticin (450 µg/ml) was used instead of Hygromycin B during selection and cultivation of the cells.
(c) Elisa of Samples Obtained from CHO Flp-In Clone 019 Cells Transfected in Bulk with the Mini Six Library The cells were cultured for 73 days post transfection and samples for ELISA were taken at day 17, 31, 45, 59 and 73. A quantitative ELISA (using individually purified mini six antibodies as standards) was performed as described (Example 3, section, f.2). The results from three independent transfections are shown in FIG. 12. Different expression profiles between different transfections were observed. However, all six antibodies were detectable in all experiments up to day 59.
(d) Conclusion from the Experiment Experiments with the Neomycin selection system on CHO Flp-In clone 019 cells showed relatively preserved expression profiles of individual batches, for two months after bulk transfection (FIG. 12). Such a period of stability is sufficient for manufacturing purposes. The batch to batch variation observed can be dealt with by generating and banking a large freezing stock of the individual batch prior to production.

Example 3B

Evaluation of Polyclonality Preservation in Cell Cultures Generated by Mixing Individually Transfected CHO Flp-In Cells after Selection
(a) Individual Transfection and Selection of CHO-Flp-In Cells The experimental procedures for generation of the six cell lines expressing the individual members of the mini six library has been described previously (Example 3, section e.3). The six cell lines expressing individual members of the mini six library were mixed immediately after selection in equal numbers ($5 \times 10^5$ of each cell line) and the mixed cell population was cultivated for 85 days. Three separate mixtures were made from the individual cell lines.
(b) Elisa of Samples Obtained from Polyclonal Cell Cultures Generated in (a)

Samples were taken every fortnight and the composition of the antibodies expressed from the mini six library was determined by ELISA as described (Example 37 section f.2). ELISA was performed at day 8, 17, 30, 45, 57, 72 and 85 after the mixing. The results (mean±SD of triplicate experiment) are shown in FIG. 13. All six antibodies were detectable 85 day post mixing. As previously mentioned (Example 3, section f.2), the readings for different antibodies were not directly comparable but data presented in FIG. 13 shows relatively stable expression profiles at least up to day 45 after mixing, after which a general drop in productivity is observed. Furthermore, comparison of results obtained from three independent mixes showed similar expression profiles over time of the mini six antibodies indicating that the results were reproducible.
(c) Conclusion from the Experiments Polyclonal cell cultures composed of mixtures of cells transfected individually with distinct members of the mini six library showed compositional preservation at least up to day 45 after mixing. A compositional preservation for 45 days will in most cases be sufficient time for manufacturing purposes. Furthermore, triplicate experiments gave similar results, thereby indicating that mixing of cells transfected individually with different constructs results in mixed cell cultures with low batch to batch variation.

Example 4

Establishment of an Anti-Ovalbumin Recombinant Polyclonal Antibody Manufacturing Cell Fine
(a) Expression of an Anti-Ovalbumin Polygonal Antibody Composition A collection of fully characterized ovalbumin-binding phage clones has been identified as follows. Four eight-week old female BALB/c mice were immunized i.p. and s.c. with 50 µg OVA in complete Freunds Adjuvant and boosted with OVA in incomplete Freunds adjuvant at days 21 and 42 after immunization day 0, and it was confirmed that all animals had sera converted against OVA, as measured by an antigen-specific ELISA. Spleens were harvested from the best responding mice at days 31 and 52. Fab-displaying phagemid libraries were generated from splenic RNA, using the phagemid vector (Symvc10) as previously described. The resulting libraries contained approximately $10^6$ independent clones. Selection of these libraries was performed by reacting $5 \times 10^{11}$ Fab-displaying phagemids with OVA coated on NUNC immunotubes, followed by washing and acid elution of binding phages. As eluates from the first round of panning contained a significant proportion of OVA binders, eluates from first and second rounds of panning were screened for OVA-binding phage clones.

Initially, OVA-reactive phage clones were identified by ELISA. In brief, ELISA plates were coated with OVA and reacted with the phage-displayed Fabs, followed by an HRP-conjugated secondary antibody. For negative controls, irrelevant antigens (BSA) or irrelevant phage-displayed Fabs (anti-AP) were used.

In addition, a HDS method, based on OVA immobilization on PVDF membranes, was established. These two methods resulted in the identification of separate subsets of clones, i.e. some clones that recognized OVA in one set-up and not in the other and vice versa. For Fab-displaying phage clones that reacted with OVA by either ELISA or HDS, the nucleotide sequence encoding the variable domain of the $V_H$ was determined by DNA sequencing, and the genetic diversity was estimated by phylogenetic analysis, using the Vector NTI software package. The resulting panel includes 127 OVA-binding clones, for all of which the nucleotide sequences of the variable part of the $V_H$ have been established.

Fab fragments expressed by the 127 OVA-binding clones all have the ability to bind to ovalbumin either in native or denatured form. From this set we have identified approximately 30 different clones contained in a phagemid vector, e.g., pSymvc10, to be used for mass transfer and mammalian expression. These antibodies are expressed either in the form of mouse IgA, IgG2A or IgG2B antibodies. Because we have fully characterized the DNA sequences of these antibody producing clones, we are able to monitor the distribution of the genotypes throughout the mass transfer and mammalian expression procedure using the same methods as used for the model system with the six distinct antibodies described in example 3.

(b) Mass Transfer of the OVA-Specific Antibody Sequences to a Vector for Mammalian Expression The transfer of genes of interest from a phagemid vector to an expression vector is a two step procedure (illustrated in FIG. 4), where the first step, is exchange of promoters with the promoter cassette with head-to-head orientation of the selected mammalian promoters, this is followed by transferring the variable region of the genes of interest and the promoter cassette to an expression vector. The head-to-head promoter cassette (promoter A/promoter B) can be inserted into the phagemid vector of each clone by using a SacI/XhoI digest followed by a ligation resulting in exchange of promoters from bacterial to mammalian promoter (pSymvc12).

An EcoRI and NotI digest will then move the sequences encoding the variable heavy chain, the head-to-head promoter cassette (promoter A/promoter B) and the complete kappa chain from the phagemid vector (pSymvc12) into an isotype-encoding vector, pSymvc20. The pSymvc20 vector can accept any NotI/EcoRI fragment from the phagemid vector. This fragment would transfer the sequence encoding the variable heavy chain to connect with the constant heavy chain sequences in pSymvc20 as well as the entire sequence encoding the kappa chain to be connected with bGH PolyA sequence. This mass transfer will result in expression vectors as shown in FIG. 1, which express the variable heavy regions and the entire kappa chains as mouse IgG2B antibodies after the mass transfer.

The vector, pSymvc20, can contain the mouse constant regions of the heavy chain of the IgA, IgG2A, IgG2B, IgE or IgG1 genes, and is thus capable of expressing any of the relevant mouse immunoglobulin isotypes of choice.

(c) Expression of an Anti-Ovalbumin Recombinant Polyclonal Antibody

By mass transfer, the sequences encoding the variable region of the heavy chain, the promoters and the entire kappa chain are moved from a phage vector library to isotype-encoding vectors resulting in a polyclonal mammalian expression vector composition. This is followed by transfection and site-specific integration into a CHO-Flp-In cell line, generating a recombinant polyclonal antibody manufacturing cell line. This latter cell fine is generated by targeting the gene of interest encoding each member of the recombinant polyclonal protein into the same specific location in the genome of each transfected cell, and at the same time integrating only one copy of the expression construct containing said nucleic acid sequence in each transfected cell.

The cell cultures and the transfection and selection procedure is the same as described in example 3 (e.1-e.3).

(d) Monitoring Composition Stability

To ensure that the mass transfer and transfection into mammalian cells occur without introduction of considerable bias with regard to cloning, expression and diversity among the individual clones the process of mass transfer and mammalian expression can be monitored with the following methods:

1) Analysis of generation time of the pools of cells from each transfected construct,
2) Analysis of expression level of the pools of cells from each transfected construct,
3) Analysis by RFLP on single cells,
4) ELISA of the produced antibody mixture,
5) Mass spectrometry of the produced antibody mixture,
6) Analysis by Taqman PCR (real-time PCR) on a defined batch size using V region-specific primers to identify ratio's of each different clone, or
7) Analysis of the batch over time cultivated with and without selection pressure (hygromycin) can be performed for the following parameters.
   a) clonal distribution
   b) protein expression levels (quantity and distribution)
   c) genomic stability
   d) effects of adaptation to serum-free media.

(e) Production of an Anti-Ovalbumin Recombinant Polyclonal Antibody Composition

The recombinant polyclonal antibody producing CHO-Flp-In cell line is grown in different culture systems, including conventional small culture flasks, Nunc multi layer cell factories, and small high yield bioreactors (MiniPerm, INTEGRA-CELLine). Further, the cell lines are adapted to serum free suspension for subsequent cultivation in spinner flasks, hollow fibers, and bioreactors.

The media used to grow the selected cell lines are serum free, protein free or chemically defined media as recommended by the manufacturer (Invitrogen, B&D, Hyclone).

Supernatants from attached or suspension cells that are cultured without selection (hygromycin) are collected. The collected supernatants are analyzed and characterized as described (3f). Production yields, functionality, and quality of the produced antibodies are checked during and after growth of the cells under fed batch or perfusion conditions. Cells in suspension are used for inoculation of larger spinner flasks or bioreactors.

The polyclonal antibody from the collected supernatants is purified for later use in animal studies.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

The invention claimed is:

1. A method for the manufacture of a pharmaceutical composition comprising a plurality of antibodies, comprising:
   a) providing a plurality of individual recombinant cell lines, each cell line comprising cells capable of expressing one of said antibodies, wherein each antibody is encoded by a nucleic acid sequence located at the same single site in the genome of said cells;
   b) mixing said individual recombinant cell lines to provide a recombinant polyclonal cell line;
   c) culturing said recombinant polyclonal cell line to obtain expression of said antibodies;
   d) purifying said antibodies from the cultured cells or the supernatant of the cultured cells; and
   e) preparing a pharmaceutical composition by combining the purified antibodies and a pharmaceutically acceptable excipient.

2. The method according to claim 1, wherein expression levels of the nucleic acid sequences encoding the antibodies are monitored by monitoring levels of mRNA or protein.

3. The method according to claim 2, further comprising
   measuring expression levels of individual antibodies at a first time point during the culturing step, thereby determining a baseline value for the relative expression levels of said individual antibodies,
   measuring expression levels of said individual antibodies at further time points during the culturing step, thereby determining the relative expression levels of said individual antibodies at each of said further time points, and
   terminating the culturing step if the relative expression levels of said individual antibodies in the culture changes from said baseline value.

4. A method for the manufacture of a pharmaceutical composition comprising a plurality of antibodies, in a single bioreactor comprising:
   a) providing a plurality of individual recombinant cell lines, each cell line comprising cells capable of expressing one of said antibodies, wherein each antibody is encoded by a nucleic acid sequence located at the same single site in the genome of said cells;
   b) mixing said individual recombinant cell lines to provide a recombinant polyclonal cell line;
   c) culturing said recombinant polyclonal cell line in a single bioreactor to obtain expression of said antibodies;
   d) purifying said antibodies from the cultured cells or the supernatant of the cultured cells; and
   e) preparing a pharmaceutical composition by combining the purified antibodies and a pharmaceutically acceptable excipient.

5. The method of claim 1, wherein the cells are mammalian cells.

6. The method of claim 5, wherein the mammalian cells are selected from the group consisting of Chinese hamster ovary (CHO) cells, COS cells, BHK cells, YB2/0 cells, NIH 3T3 cells, myeloma cells, fibroblasts, HeLa cells, HEK 293 cells and PER.C6 cells.

7. The method of claim 4, wherein the cells are mammalian cells.

8. The method of claim 7, wherein the mammalian cells are selected from the group consisting of Chinese hamster ovary (CHO) cells, COS cells, BHK cells, YB2/0 cells, NIH 3T3 cells, myeloma cells, fibroblasts, HeLa cells, HEK 293 cells and PER.C6 cells.

9. The method of claim 1, wherein the recombinant polyclonal cell line is cultured in a single bioreactor.

10. The method according to claim 2, wherein expression levels of the nucleic acid sequences encoding the individual antibodies are monitored by monitoring levels of mRNA.

11. The method according to claim 2, wherein expression levels of the nucleic acid sequences encoding the individual antibodies are monitored by monitoring levels of protein.

12. The method of claim 4 or 9, wherein the bioreactor is between 30 and 100 liters in capacity.

13. The method of claim 4 or 9, wherein the bioreactor is larger than 100 liters in capacity.

* * * * *